(12) United States Patent
Wolgin

(10) Patent No.: US 11,191,623 B2
(45) Date of Patent: Dec. 7, 2021

(54) NEGATIVE PRESSURE WOUND THERAPY FOR TREATMENT OF PERIODONTAL DISEASE

(71) Applicant: Mark Wolgin, Albany, GA (US)

(72) Inventor: Mark Wolgin, Albany, GA (US)

( * ) Notice: Subject to any disclaimer, the term of this patent is extended or adjusted under 35 U.S.C. 154(b) by 887 days.

(21) Appl. No.: 15/844,976

(22) Filed: Dec. 18, 2017

(65) Prior Publication Data

US 2018/0104034 A1   Apr. 19, 2018

Related U.S. Application Data

(63) Continuation of application No. 15/442,610, filed on Feb. 24, 2017, now Pat. No. 9,855,123, which is a continuation of application No. PCT/US2016/056291, filed on Oct. 10, 2016.

(60) Provisional application No. 62/240,313, filed on Oct. 12, 2015.

(51) Int. Cl.
*A61C 17/02* (2006.01)
*A61M 1/00* (2006.01)
*A61C 17/08* (2006.01)
*A61C 19/06* (2006.01)

(52) U.S. Cl.
CPC ...... *A61C 17/0211* (2013.01); *A61C 17/0208* (2013.01); *A61C 17/08* (2019.05); *A61C 19/063* (2013.01); *A61M 1/962* (2021.05); *A61M 2205/07* (2013.01); *A61M 2205/8206* (2013.01); *A61M 2210/0631* (2013.01)

(58) Field of Classification Search
CPC . A61C 17/0208; A61C 17/0211; A61C 17/08; A61C 19/063; A61C 19/066; A61M 2205/07; A61M 2205/071; A61M 2205/076; A61M 2205/8206
See application file for complete search history.

(56) References Cited

U.S. PATENT DOCUMENTS

| | | | | |
|---|---|---|---|---|
| 3,731,675 | A  * | 5/1973 | Kelly | A61C 17/0211 601/164 |
| 5,104,315 | A  * | 4/1992 | McKinley | A61C 17/0211 433/216 |
| 9,308,064 | B2 * | 4/2016 | Binner | A61C 17/0208 |
| 9,968,335 | B2 * | 5/2018 | Binner | A61B 5/682 |
| 2002/0110780 | A1* | 8/2002 | Zegarelli | A61K 9/0063 433/80 |
| 2006/0096600 | A1* | 5/2006 | Witt | A61M 16/0009 128/848 |
| 2011/0027746 | A1* | 2/2011 | Mcdonough | A61C 17/0211 433/80 |
| 2014/0072931 | A1* | 3/2014 | Fougere | A61C 17/0211 433/80 |
| 2017/0151400 | A1* | 6/2017 | Vaska | A61M 16/0463 |

* cited by examiner

*Primary Examiner* — Kim M Lewis
(74) *Attorney, Agent, or Firm* — Brainspark Associates, LLC

(57) ABSTRACT

Disclosed are devices, systems and methods for treating periodontal disease and/or other oral wounds using particularized oral appliances and associated negative pressure systems. The various oral appliances include one or a plurality of surfaces for engagement with various anatomical structures within the oral cavity, where the engagement can include sealing engagement with soft tissue (gingival) surfaces of the upper and/or lower dental arches. Additional features disclosed can further promote healing of regions affected by periodontal pocket formation.

20 Claims, 27 Drawing Sheets

NEGATIVE PRESSURE WOUND THERAPY FOR TREATMENT OF PERIODONTAL DISEASE

CROSS-REFERENCE TO RELATED APPLICATIONS

This application is a continuation of U.S. patent application Ser. No. 15/442,610 entitled "Negative Pressure Wound Therapy for Treatment of Periodontal Disease," filed Feb. 24, 2017, which in turn claims the benefit of PCT Patent Application Serial Number PCT/US16/56291 entitled "Negative Pressure Wound Therapy (NWPT) for Treatment of Periodontal Disease," filed Oct. 10, 2016, which in turn claims priority to U.S. Provisional Patent Application Ser. No. 62/240,313 entitled "Negative Pressure Wound Therapy (NWPT) for Treatment of Periodontal Disease," filed Oct. 12, 2015. Each of these disclosures are incorporated by reference herein in their entireties.

TECHNICAL FIELD

This invention relates generally to systems, devices and methods for applying suction and/or continuous or intermittent negative pressure to the oral cavity of a patient for treating conditions affecting soft tissue structures within the mouth, but most commonly those involving the soft tissues at the base of the teeth (gums/gingival tissue). Conditions affecting these tissues fall most commonly into the category of periodontal disease. More specifically, the invention is directed at systems and methods for treating or eliminating recesses that form at the junction of the tooth base and the gingival tissue, where the separation of these structures forms a potential space or pocket (referred to as periodontal pockets) in patients with periodontal disease. This type of therapy could be used both as an adjunctive treatment in the acute setting in combination with oral surgery or professional cleaning, and may also have a use on a chronic, possibly even daily, basis for disease prophylaxis (prevention). However, this invention may also have other uses in the mouth, such as healing donor graft sites, optimizing healing for a potential recipient implant site, aiding in healing intraoral wounds, or possibly even as a vehicle for delivery/concentration of medications directed to the teeth or gums.

BACKGROUND OF THE INVENTION

Gum disease, a very common ailment affecting nearly half of Americans over 30 and over 70% of those over 65, is a condition where chronic inflammation of the gums/gingival tissue can lead to discomfort and potentially to loss of teeth. Gum disease, called gingivitis (or for deeper penetration of the process—periodontitis), is usually caused by a combination of factors, including: (a) tissue qualities in the patient's mouth (usually at least partially genetically determined); (b) patient hygiene and home/professional care (i.e., brushing, flossing and dentist visits); and/or (c) various types of bacterial growth in the mouth (which can often be affected or controlled to a significant degree with proper oral hygiene).

Two salient factors that can contribute significantly to the development of periodontal disease are plaque and tartar. Plaque, a sticky bacterial film that can accumulate on the sides of teeth, not only can lead to tooth decay by increased local acid concentration, but can also irritate and cause inflammation of the gums/gingival tissue. While in most cases plaque can be removed through daily brushing, flossing, and oral rinsing, in some cases the plaque, in combination with minerals in the saliva, can form a hard, crusty build up at the base of the tooth known as tartar. This tartar, removal of which often requires professional intervention, will typically continue to calcify and irritate the gingival tissue, worsening the local inflammation. As a result of this inflammatory process, the gums can partially separate from the base of the tooth, creating pockets next to the teeth that not only expose the root of the tooth, but also create additional places for bacteria to reside. In many cases, these pockets can become too deep to be adequately cleaned by home care methods, including dental floss, ultrasonic toothbrushes, or pulse lavage irrigation.

The existence of periodontal "deep pockets" can cause a variety of symptoms, including bad breath, patient discomfort, temperature sensitivity, gum recession (i.e., longer appearing teeth), and bleeding gums, but the most insidious effects can include loss of supporting bone structure which can lead to loss of teeth. This loss of bone structure occurs as part of the reaction to chronic inflammation that occurs at the base of the pockets. Since the depth of the pocket cannot typically be adequately cleaned by patients themselves, this region remains chronically colonized with multiple forms of bacteria in a situation that clinically is essentially a chronic low grade infection. The mechanism of the destruction of bone with potential for loss of teeth involves the effects of the immune system as part of a cascade of cellular responses to this chronic inflammatory state. Cells involved in the inflammatory response cause, among other effects, release of cytokines (secretions from cells of the immune system that affect other cells) as well as other mediators, but the net effect is that both supporting bone and the periodontal ligaments (which attach teeth to bone) slowly resorb/disappear. This process continues until the source of the inflammation/infection, the bacterial plaque and any accumulated tartar that resides on the teeth, is cleaned. Given that there is lower likelihood of this chronic inflammation occurring when the bacteria have fewer anatomic locations to become sequestered, the risk of bone and tooth loss would be significantly diminished by a treatment that could decrease or limit the depth of the periodontal pocket.

Current options available to dental professionals for prophylaxis (disease prevention) and for treatment of periodontitis include (a) home care and regular dental hygiene and flossing by the patient; (b) periodic deep cleaning in a dentist's office, including scaling and root planing; (c) the application of medications to the patient's mouth, including antibiotic rinses, gels, and other delivery systems including microspheres; (d) the use of custom dental appliances impregnated with antibiotics proximate to the inflamed locations; and/or (e) the employment of various oral surgical procedures, including flap surgery. Flap surgery involves lifting the gums to remove tartar and/or deposits and allowing the surgeon direct access to the base of the tooth, and then suturing the gums back to result in significantly more shallow (less deep) periodontal pockets. In many instances this flap surgery option can result in more gum recession (i.e., there is less gum tissue left, so teeth appear longer) or the need for bone or tissue grafting (i.e., taking bone or gum tissue from elsewhere to pack into a small area to promote tissue regeneration, to allow connective tissue to re-grow).

Despite the best intentions of the dental health professionals, and good home care efforts by the patient, traditional treatments for periodontitis can slow but often not halt disease progression. Even with brushing and flossing, and even with mechanical assistance from appliances such as the ultrasound toothbrush (e.g., SONICARE) and pulse lavage (e.g., WATERPIK) devices, the depths of the pockets, especially when they get to be greater than 4-6 mm, cannot typically be cleaned thoroughly by the patient, and professional cleaning is often required. In most instances, this type of deep cleaning involves either some sort of discomfort, or administration of local anesthesia, and is not without significant cost.

Aside from the anatomical challenges of cleaning the depths of the periodontal pockets, another issue is that the chronic colonization of the pockets involves multiple forms of bacteria, and even a professional cleaning is often temporary at best. Even if a dental professional were able to get to access the bottom of the pocket and scrape it clean, that area will typically be re-colonized with bacteria almost immediately. Moreover, attempts to decrease the bacterial load in the pockets by locally applying antibiotics with dental appliances have been heretofore unsuccessful, with numerous studies showing that such medication applications do not typically reach the source of periodontal infections at the base of the tooth.

In cases of periodontal pocket formation that require surgical treatment, additional challenges exist. Aside from the patient discomfort and expense, even with flap surgery, since the mouth is not made sterile, there are persistent bacteria at the base of the flap at the time of surgery. Moreover, the gingival flaps are often repaired with sutures, which are themselves foreign bodies that cause a component of tissue reaction/inflammation, and the swelling component of the inflammatory reaction prevents egress/outflow of tissue fluids, creating further areas where bacteria can reside.

BRIEF SUMMARY OF THE INVENTION

One aspect of the present invention includes the recognition of the various issues and challenges in treating periodontal disease (as noted above), and the realization of a need for improved oral appliances and related methods and techniques to resolve issues currently presented with such traditional treatments. The present invention includes devices, systems and methods to desirably optimize the healing capabilities of inflamed tissues in the mouth to promote improved soft tissue healing using a method that can be relatively simple to apply in a manner that desirably does not involve significant patient discomfort.

As opposed to the eventual resolution that occurs with healing in an acute wound, the cellular events that occur in the setting of periodontal pocket formation typically reflect those that occur with a chronic wound. From a general perspective, successful wound healing can occur when there are more factors favorable for, rather than against, the healing process. In wounds that become chronic, the factors for and against healing reach a balance called stasis, where little changes. One factor germane to understanding non-healing wounds is that the tissue repair process requires more oxygen and nutrients than required for maintenance of tissue. Given that more circulation and cell division are required for repair to occur, the focal swelling associated with chronic inflammation can be more of a hindrance to the repair process as localized swelling can restrict blood flow to the tissues. In this state of relative hypoperfusion (i.e., less than adequate blood flow), the tissues around the wound are typically less successful at providing oxygen and nutrients needed to promote healing. Factors that would favor development of additional blood flow to the area, along with allowance of egress (removal) of excess tissue fluid, would desirably create an environment where the local tissues are also better able to fight infection and close/repair the periodontal pockets naturally with local tissue ingrowth. Similarly, factors that would decrease swelling and encourage angiogenesis (i.e., ingrowth of blood vessels to the area) would desirably favor wound healing.

The present invention, which can in various embodiments include the fabrication of a custom oral appliance to direct the application of negative pressure wound therapy (NPWT) or vacuum therapy to one or more areas within the mouth, is proposed to, among other potential uses, create more optimal conditions to allow gingival tissue to heal back to the base of the teeth, and to minimize the clinical sequelae of untreated periodontal pocket formation. In various embodiments disclosed herein, an improved oral appliance and treatment method are provided that represent significant advancements in the fight against periodontal disease. Given the relatively well perfused (i.e., good blood supply) character of typical gingival tissues, along with a generalized significant baseline of resistance to infection in these tissues (i.e., periodontal surgery in the contaminated oral environment is often done without antibiotics), the current invention could likely augment the factors affecting wound healing that desirably change cellular events in a favorable manner.

One objective of the present invention is to provide an improved oral appliance device and method that would eliminate or resolve many of the challenges experienced by dentists, oral surgeons and/or other health care professionals in their treatment of periodontitis. In at least one exemplary embodiment, a custom oral appliance can be provided that contacts at least a portion of teeth and/or soft tissues inside of a patient's a mouth to provide negative pressure to some or all of a diseased area and/or the surrounding anatomy. The negative pressure or vacuum environment will desirably create a focal or generalized pressure gradient that can draw fluids, solids and/or other exudates from a specific area of the gum tissue at the base of the teeth, or even possibly other areas within the oral cavity, and may optionally draw gum flap tissue closer to, proximate to and/or into intimate contact with some or all of the exposed teeth to facilitate healing and/or reattachment in a desired manner. This healing and/or reattachment may occur through a combination of the applied negative pressure (while using the custom oral appliance) and various natural physiological healing responses of the body. In various embodiments, the negative pressure gradient will desirably assist with removal of drainage (tissue exudate) and/or other fluids/materials from a diseased area, it may induce an angiogenic response or reaction to the localized gum tissue layers to potentially create new microvasculature for improved waste removal and/or blood flow, and it may induce mitosis (i.e., cell division) to repair/replace damaged tissue and/or enhance attachment of the gum tissue to the exposed teeth.

In one exemplary embodiment, the improved negative pressure dental system comprises a custom oral appliance, a single or multi-lumen tube system, and a source of negative pressure (i.e., a vacuum machine).

In another exemplary embodiment, the custom oral appliance may comprise an upper and/or lower custom oral appliance which covers some or all of the dentition/dental arches, and which can be manufactured at least partially from a polymeric material. The custom oral appliance can include an inner contact surface and an outer surface. The inner contact surface could desirably be in contact with some or all of the teeth, gingival (gum) tissue, and/or palate, and the outer surface could be in contact with various other tissues within the mouth such as the tongue (lingual surface), the cheeks (buccal surface), and/or the lips (labial surface), depending on the structural aspects of the patient's individual appliance. The negative pressure environment could be applied to the tissues in contact with the inner surface of the appliance, which could include equal and/or unequal negative pressure application (i.e., include pressure transfer across the teeth due to the spaces between the teeth), and/or the equal/unequal distribution of pressure could be provided by a channel or other feature created along a margin of the tooth and gum (commonly referred to as the gingival sulcus), or other desired area, depending on the location of the intraoral condition being treated (with one example being to facilitate healing from a soft tissue donor site in the palate for gingival repair via soft tissue grafting). The application of negative pressure proximate to the gingival sulcus would desirably serve several functions in the treatment of periodontal pockets, including reducing local tissue edema, removing tissue fluids from the depths of the pockets, and/or providing a pressure gradient for bringing healing cells to this region.

Various embodiment can include methods of fabricating an oral appliance with a channel or void facing towards and/or positioned proximate to a targeted anatomical surface, such as a surface of the tooth and gums at the level of the gingival sulcus. Desirably, features can be provided that reduce and/or eliminate the vacuum pressure in the appliance during device removal, such as pressure release valves and/or flexible tabs on the appliance and/or tubing, which would desirably make the appliance easier for the patient to apply and/or remove. If desired, there may be at least one aperture that extends from the front of the appliance for the application/delivery of negative pressure to the inner surface of the appliance. In various embodiments, the polymer(s) utilized in manufacturing the appliance (if any) will desirably not exhibit any odor or taste, can be substantially flexible and will desirably contain proper tensile and/or impact properties. The polymeric material may also be made clear or opaque.

In another exemplary embodiment, a single-lumen or multi-lumen tube system may include an oral appliance tube adapter, a single or multi-lumen tube, a transition tube, a transition adaptor, and a negative pressure tube adapter. The oral appliance tube adapter may be attached and/or connected to the oral appliance and may contain at least one or more lumina (i.e., longitudinally extending openings through and/or within the tube) to extract the exudates/tissue fluids and/or deliver the negative pressure surrounding the oral appliance, which in various embodiments may include a capability to monitor the level of pressure being applied (i.e., through one or more ancillary lumen or lumina). The transition tube may be a different size, configuration and function than the multi-lumen or single-lumen tube (i.e., one of the functions of the transition tube may be to connect to the negative pressure machine to the appliance). The transition adaptor may be a component that facilitates the transition between the multi-lumen tube to the transition tube.

In another embodiment, the negative pressure vacuum machine may be equipped with custom features or a commercially available negative vacuum machine may be used. For example, a commercially available portable suction machine can be used, such as the Medline Vac-Assist Suction Aspirator (Medline Industries, Inc. of Mundelein, Ill.). Although Medline is one example, many hospitals carry various vacuum machines of many different manufacturer types, which may also be suitable for use with the present invention, as well as permanently installed vacuum systems (which often include access ports proximate to multiple hospital beds). The portable suction machine may include minimal controls such as delivering a negative pressure range of 25-250 mmHg, can have continuous and/or intermittent operation, can carry a stored power supply and/or be rechargeable, and will desirably be of a low weight (i.e., approx. 5 lbs. or less to 25 lbs.). Alternatively, a custom negative vacuum machine may be modified to improve portability, to use battery power, to be designed for single use, and/or to be lightweight in order to make the application of negative pressure therapy less cumbersome.

In another embodiment, the negative pressure oral system may comprise an important part of a treatment program for periodontitis. After a dental professional confirms the diagnosis of periodontitis or periodontal pocket formation in a patient, one iteration of implementing this treatment strategy could include obtaining an impression of a patient's upper and/or lower teeth, and then creating a cast of a patient's upper and/or lower teeth from which the oral appliance could be fabricated. In order to focus the application of negative pressure to the gingival sulcus, a channel could be created in the appliance by applying a type of periodontal dressing to the gingival sulcus of a patient's dental cast (i.e., the model of the patient's dentition) with a focus on the areas to be treated, whether upper and/or lower arch, and whether lingual and/or buccal surfaces, fabricating an oral appliance corresponding perfectly or at least partially to the patient's individual anatomy. This appliance, which could be connected by a single or multi lumen tube(s) to a negative pressure machine with adjustable settings, could function to create a negative pressure environment as described herein to desirably optimize the local periodontal tissue conditions to maximize the chances of removing exudate from the pockets and allowing the negative pressure gradient to bring healing cells into the area. A controlled negative pressure environment could have utility in effecting healing of the periodontal pockets, but also could be used in conjunction with other oral surgical procedures such as root canals and/or placement of mandibular anchors or implants, healing of donor sites from where tissue is harvested for gingival grafting procedures, and/or could also have a use in a prophylactic capacity (i.e., disease prevention) whereby intermittent regular use, possibly combined with rigorous home care, could lead to either improvement of or prevention of a worsening of periodontal pocket formation.

In various embodiments, the devices, systems and methods described herein could have utility for use the first few days after a routine scaling, where the roots of the teeth have just undergone mechanical plaque removal, and the process of scaling may have caused a low level of trauma to the gingival tissues. Application of the negative pressure system acutely after this scaling, in the setting of the gingival tissues healing from the manipulations of the cleaning process, could optimize the healing process and lead to a decrease in pocket depth, the achievement of which is the goal of flap surgery.

In other embodiments, such as alluded to above, the negative pressure oral systems, devices and methods described herein may have particular utility in the treatment of oral wounds resulting from injuries and/or surgical procedures, including wounds resulting from root canal surgery, dental implantation procedures, graft donor sites and/or dental grafting procedures. If desired, the oral appliances described herein may be utilized to prepare an area for surgery and/or cleaning (i.e., to reduce inflammation and/or control infection in tissues targeted for surgery or cleaning and/or adjacent to intended surgical sites) as well as to treat and/or manage surgical sites after surgical procedures. If desired, the various teachings described herein may be utilized in treating surgical anchor implant sites and/or grafting sites, where healing of the site is desirous prior to final implantation of a surgical implant and/or graft, as well as after the surgical procedure to promote healing of affected tissues. Another potential benefit of using the oral appliance may be that, during the period of use, there could be a potential for the system to include features that modify neuromuscular feedback that could possibly minimize bruxism (involuntary jaw clenching) that untreated could have a deleterious effect on the periodontal ligaments (that attach the teeth to the bones).

DETAILED DESCRIPTION OF THE INVENTION

Given that negative pressure wound therapy has shown great utility in treatment of acute and chronic wounds and of burn injuries of the torso and extremities, the present invention seeks to incorporate similar benefits of therapies involving negative pressure environments to effect healing in the oral space. The application of negative pressure in the various manners described herein can desirably act to convert a chronic static situation (where periodontal pockets can be thought of a chronically infected tissue) into one with greater healing potential, and does so in a manner that is relatively comfortable for the patient to tolerate, and could help patients avoid surgical procedures that are potentially painful and expensive. The principals of negative pressure wound therapy, which have shown great effectiveness in wounds that are particularly challenging, such as in poorly vascularized tissues in orthopedic wounds with exposed tendon, bone, and cartilage, in combination with specially designed and/or constructed orthoses to direct and/or concentrate such therapies in one or more desired locations, show significant promise to treat the oral cavity. Such therapies can desirably employ negative pressure (i.e., a partial or full vacuum) to function to remove drainage (i.e., tissue exudate), while the negative pressure forms a gradient, bringing healing cells into the wound, and promotes angiogenesis (formation of new blood vessels) in one or more treated areas. Aside from removing tissue exudate, the negative pressure may also encourage wound contraction (i.e., bringing wound edges together), a process that effectively reduces the number and/or size of places that might be favored for unwanted bacterial growth.

Figure 1:
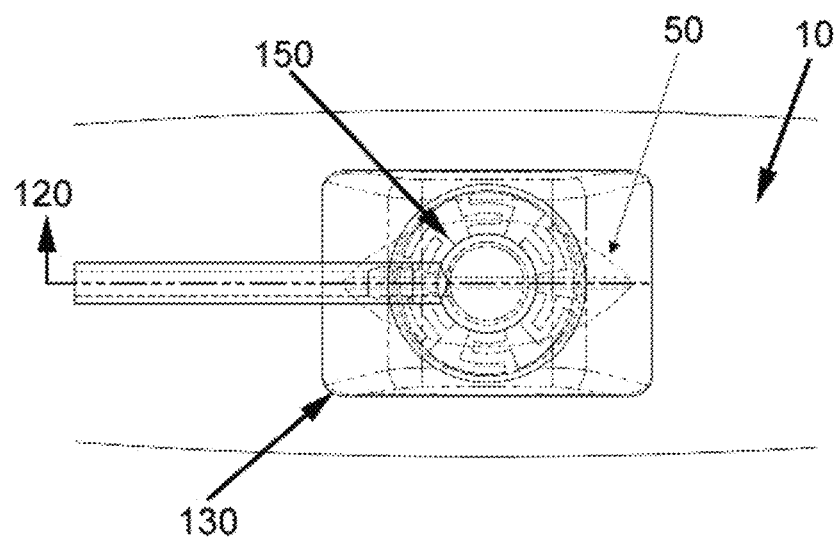
FIG. 1 depicts a top view of one embodiment of a negative pressure wound therapy on a limb.
Figure 2:
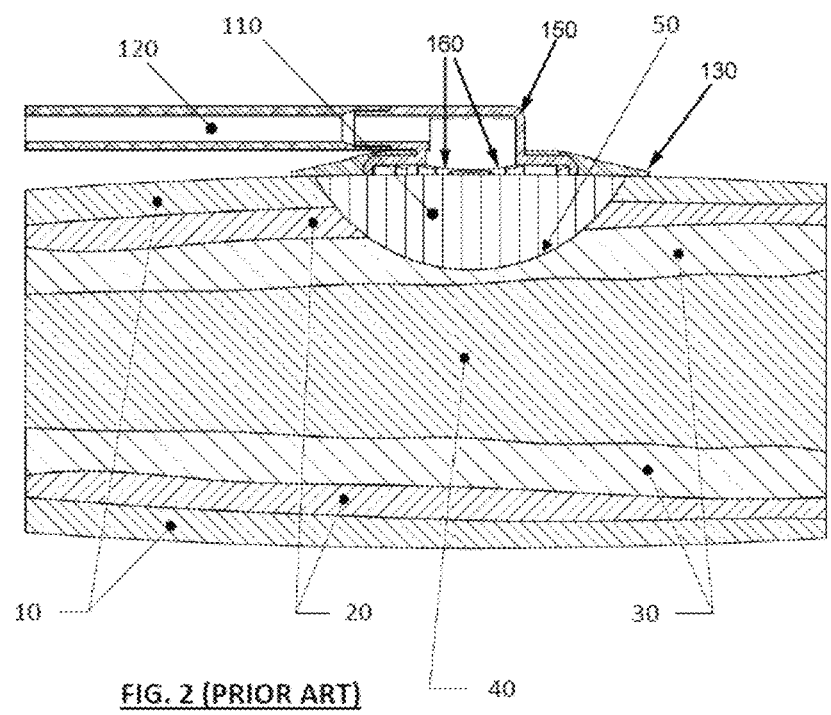
FIG. 2 depicts a cross-sectional view of one embodiment of a negative pressure wound therapy on a limb.

FIGS. 1 and 2 depict a relatively simplified view of a wound surface and associated prior art negative pressure therapy appliance, currently used for treatment of externals wounds of an extremity such as an arm or leg. The external view of FIG. 1 shows a skin surface 10, an elliptically shaped (in this case) wound 50, an adhesive dressing 130, and a trackpad or semi-rigid pad 150 for application of negative pressure outside the dressing 130, and the path of egress of any withdrawn fluids, and through which the negative pressure is applied. This exemplary extremity on a cross-sectional view includes skin surface 10, which overlies fat layers 20, which in turn typically covers muscle layers 30, with an underlying core layer of bone 40. A wound surface 50 in FIG. 2 is shown in this schematic extending deep only to a muscle layer. However, in cases where NPWT has effected healing in the extremities and torso, this wound surface can extend deep to tissues with less circulation that are harder to heal, like tendon, bone 40, and/or cartilage.

These wound surfaces would typically be present after debriding tissues that are clearly non-viable (since even negative pressure cannot often not bring them back to viability), and this schematic is offered as a way to clarify how negative pressure can be applied to a wound surface. After debridement of the non-viable tissues, there is usually a component of inflammation, which is the cascade of cellular events whereby the body mobilizes its defenses to both fight infection and to heal tissues locally. Since there is more often than not bacterial contamination, if not frank infection, usually a course of antibiotics is required. However, after the non-viable tissues (which are places where bacteria can reside) are removed, and usually after a limited course of antibiotics, healing in the negative pressure environment can often continue without and independent of antibiotic therapy. A successful treatment using NPWT, for example, could be demonstrated by the surface of the wound being eventually covered with a reddish tissue called granulation tissue (for an example of this healing, see FIGS. 3B and 3C). If further tissue necrosis has occurred (for example, if another piece of bone or tendon at the depth of the wound has become necrotic/non-viable), the granulation tissue will typically not cover the necrotic surface and repeated debridement will often be needed.

As noted above, after debridement, a suitable negative wound pressure therapy device can be applied to the wound. As best seen in FIG. 2, an existing NWPT device, pictured in cross-section, can be placed against the wound surface 50, with a significant portion of the wound adjacent to a pressure distribution member 110 (in this case a spongy foam material) which desirably transfers the vacuum pressure from a delivery tube 120 to the underlying wound surface 50. Desirably, the pressure distribution member 110 will comprise a flexible material having an abundance of open cells and/or air passages (i.e., an open cell, "spongy" surface), which allows the vacuum pressure to be transferred and applied evenly to large areas of the wound surface 50 without drawing the delivery tube 120 and wound surface 50 into direct contact with each other. The member 110 in this embodiment could be selected and/or shaped to desirably fit approximately into the wound cavity and to evenly distribute the negative pressure environment. An adherent dressing 130 can be placed on top of the member 110 and surrounding skin surface 10. The adherent dressing 130 will desirably comprise an airtight material, which in this embodiment could be a thin film material which is desirably flexible and sticky on at least one side. The adherent dressing 130 can be applied to the skin surface 10, to seal in the wound environment, with a small hole (not shown) made in the adherent dressing. A semi-rigid pad 150 (i.e., a "trackpad," commercially available from Acelity L.P., Inc. of San Antonio, Tex., USA) can be placed over the small hole in the adherent dressing, providing an air tight connection between the delivery tube 120 and the member 110, which desirably applies the negative pressure to the wound. The net effect of this arrangement is that the surfaces of the wound in contact with the spongy member 110 are desirably subject to a generally uniform vacuum pressure, without significant concentration of vacuum in any specific area. While this information is provided for perspective on how negative pressure is typically applied to a generic extremity wound, including the requirement for both an adherent dressing to maintain the suction seal for negative pressure, and for a sponge to equally distribute the negative pressure over the treatment surfaces, some or all of these elements may not be required for treatment of wounds within the oral cavity, as will be detailed below.

In wound applications of this generic type, the use of such spongy materials is extremely important to the proper application of wound therapy. Without the spongy intermediate material, the direct application of vacuum pressure from the trackpad to the underlying wound surface would typically concentrate an excessively high vacuum pressure to a small area of the wound bed, and likely draw some portion of the damaged tissues into the opening 160 of the trackpad, which would further exacerbate and compromise the wound. Moreover, the negative pressure applied through the hole would not be properly distributed to the remainder of the wound surface (i.e., to areas not under the hole). As noted above, in the present invention, since the teeth can potentially act as a scaffold for various embodiments, and since the moist surfaces in the mouth are optimal for forming a seal, the spongy material may not be needed in various embodiments.

Negative pressure wound therapy can be used in a number of wound settings that would ordinarily be challenging to address. In many instances the wound environment is "challenging" because of the presence of significant amounts of necrotic tissue (which will often require debridement) in various locations within or surrounding the wound. Healing can also be challenging due to other factors including the presence of minimal local blood supply, significant wound depth with potential for drainage issues, and the limited availability of local tissues for potential transfer to fill the post debridement defect.

Figure 3A:
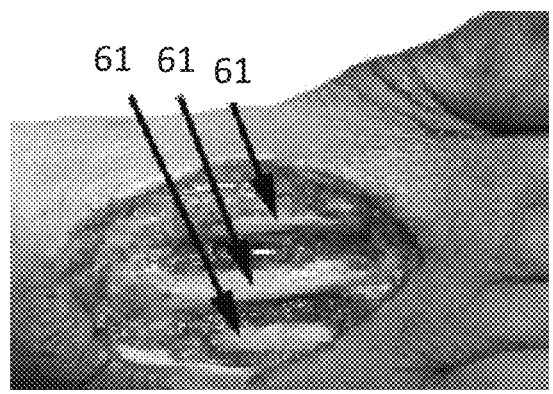
FIGS. 3A through 3C illustrate an exemplary time healing response of an extremity wound using negative pressure wound therapy.
Figure 3B:
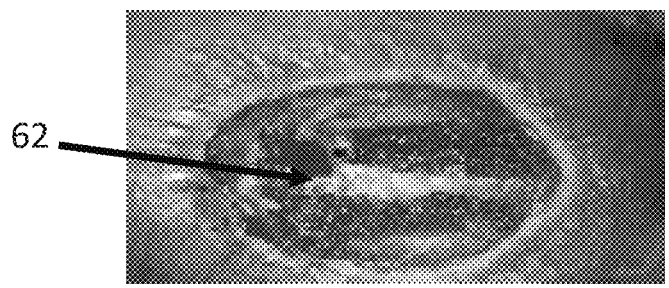
Figure 3C:
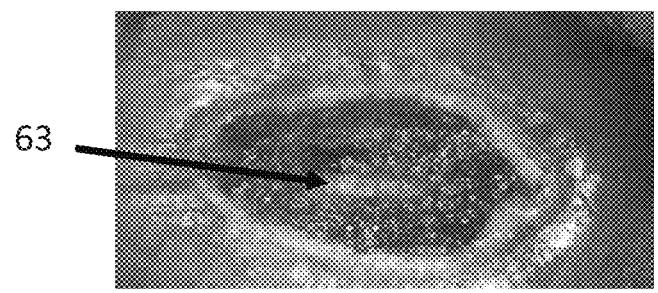

To illustrate how NPWT can be very useful in wound environments that are challenging, consider the example illustrated in FIGS. 3A through 3C of a wound on the dorsal aspect of a foot which, after debridement of non-viable tissues, shows exposed bone, which is a poorly vascularized tissue type. The options for salvage of the type of foot wound illustrated would be extremely limited, and absent NPWT, salvage of the foot as pictured would be unlikely to occur. After debridement, a sponge was cut to fit the contour of the wound, and it was placed over the wound. Subsequently, an adhesive dressing was applied over the contoured sponge and a track pad (as described above) was applied to a small hole made in this adhesive dressing. Through the application of negative pressure to this wound surface, tissue exudates were removed, and a gradient was created to draw healing tissues to the surface, thus allowing for tissue growth to occur over the exposed bone with healing documented in the interval figures of 3A through 3C. With particular reference to FIG. 3A, exposed metatarsal bones 61 can be seen after debridement, with healing evident at three weeks post treatment (i.e., partially exposed metatarsal bones 62 of FIG. 3B) and at five weeks post treatment (i.e., see minimally exposed metatarsal bones 63 of FIG. 3C).

Alternative treatment options for the type of wound shown in FIG. 3 are typically suboptimal. For example, limitations of other treatment options could include: (1) local tissue transfer is limited by the availability or lack thereof of local tissue; (2) free tissue transfer could require a plastic surgeon to perform this type of procedure, a service increasingly difficult to arrange and reimbursed either poorly or not at all by insurance companies, and could leave the patient with a sometimes unsightly tissue mass on the dorsal foot; or (3) the application of moist dressings and "hope" that some healing can occur before the bone becomes non-viable—a technique that is rarely successful. There are countless instances where NPWT has provided for limb salvage in extremity wounds.

Some wound situations are more challenging than others for healing to occur. Especially in situations with poor local blood flow, the normal physiologic responses, absent modalities like negative pressure wound therapy or other more aggressive, costly, and potentially painful surgical techniques, can be ineffective in bringing about healing. Fortunately, with regards to the current invention, since there is better vascularity of gingival tissues, the currently described invention would likely be effective with a treatment schedule that requires patient participation for significantly less time than is required for wounds of the extremities and torso. For reference; gingival flap surgery usually demonstrates adequate healing in 5-7 days, so shorter intervals of NPWT could significantly optimize healing of such wounds in the oral environment.

Various embodiments of the present invention include devices and methods of use that seek to apply various advantages of negative pressure wound therapy in a unique and unusual manner to one or more periodontal applications. While many wounds in the oral cavity may have the capacity to heal faster and with less scarring than similar wounds in other parts of the body, the healing of some tissues in the mouth, especially the repair and/or regeneration of tissues at the base of a periodontal pocket, are more difficult.

Figure 4A:
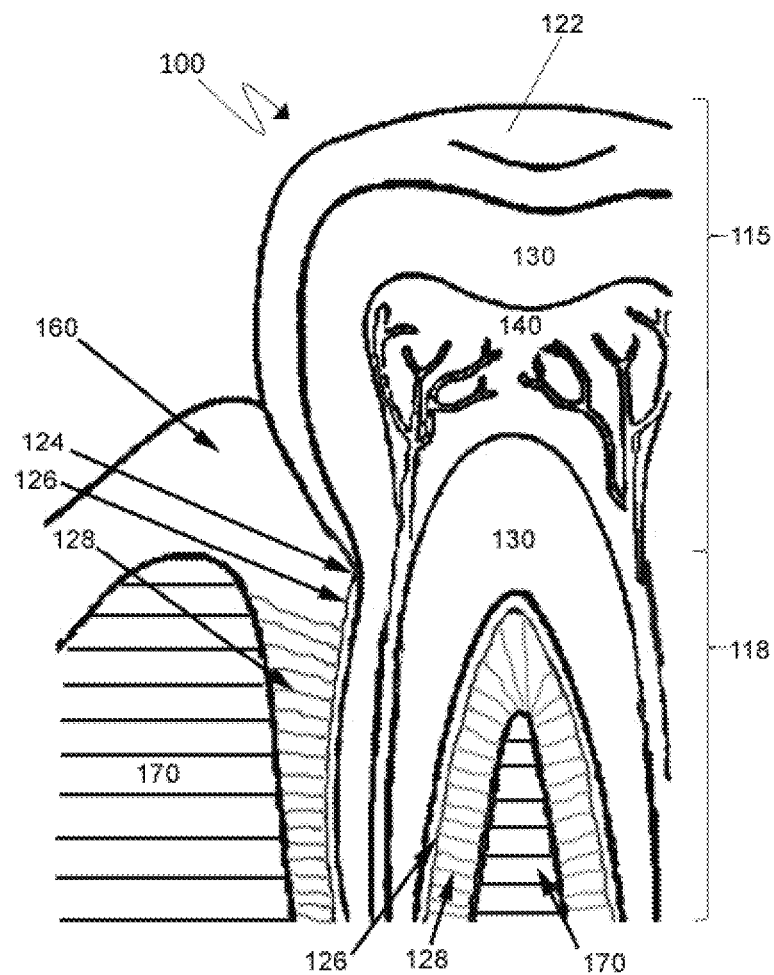
FIG. 4A illustrates a partial cross-sectional view of one embodiment of a healthy tooth and adjacent gum tissues.

Periodontal tissues include a variety of types, including soft and mineralized tissues which form the connection between the teeth and the underlying bony structures. Many of these structures are illustrated in FIG. 4A. The tissues that cover a surface are called epithelial tissues, and epithelial cells are on the surface of the gingival tissues, and also line the periodontal pockets when they form. The periodontal ligaments (FIG. 4A, 128) are connective tissue structures including neural and vascular elements that connect the cementum covering the tooth root (FIG. 4A, 126) to the alveolar bone (FIG. 4A, 170). This connection is referred to as the dentogingival junction, and maintaining its integrity is essential in order to preserve the periodontal ligaments which anchor the teeth to the bone. However, this junction is often damaged and/or destroyed by the chronic inflammatory process related to periodontal diseases, and in order to effectively control the destructive effects of chronic periodontal diseases and to regenerate the lost tissues to some degree, the dentogingival junction will desirably need to either be restored, or to have tissue loss mitigated.

In cases of chronic periodontitis, the dueling forces of bacterial colonization/chronic infection vs. the immune/healing response of the body are at a standoff, with little improvement left untreated. However, beginning the repair process usually involves professional cleaning/scaling of tooth surfaces in the depths of the periodontal pockets. As a response to this cleaning, the tissues are often irritated causing a temporary increase in inflammation, and as a result, the cellular events involved in wound healing are amplified. In the acute setting as such, a number of aspects of the inflamed tissues can be modified by application of NPWT to optimize healing potential as described herein. The irritated/wounded tissues become more permeable, and in many instances where some bleeding has occurred, clot forms. Inflammatory cells invade the area, and a cascade of cellular events occur, including the migration of fibroblasts into the area, along with angiogenesis, formation of new blood vessels, from endothelial cells that migrate in from adjacent broken blood vessels. These healing cells form a tissue called granulation tissue (in a manner similar to the tissues repairs depicted in the foot example in FIGS. 3A through 3C, but typically on a smaller scale in gingival tissues). Next, the migration of epithelial cells covers the denuded tissue surfaces or forms a junction at the tooth-tissue interface. Lastly, maturation of the healing tissue matrix can be accompanied by contraction or scarring. NPWT can function in these situations to allow for increased egress of tissue fluids, decreased edema, and the negative pressure gradient can increase angiogenesis.

The healing potential of periodontal pockets, while influenced by multiple factors, is also related to the depth of the process. The level of the alveolar bone is referred to as the crest of the bone (FIG. 4A, 170). A periodontal pocket that goes above the bone (supracrestal) is generally less severe than one that goes below the level of the bone (subcrestal), but also different tissue types can be involved.

Gingivitis is described as the inflammation that is limited to the gingival tissue, not extending below the crest of the alveolar bone (FIG. 4C, 127) with this level demarcated by crestal periodontal ligament fibers. At this level of disease, there is less disturbance to the soft tissues supporting the cementoenamel junction. These anatomical structures are illustrated in FIG. 4A, showing the cementum 126 which covers that anatomic root of the tooth, along with the cementoenamel junction 124 which is where the enamel meets the cementum, and the periodontal ligaments 128 which help anchor the tooth to the underlying alveolar bone. If gingiva is removed by surgical excision, granulation tissue and epithelial cell migration from the adjacent mucosal tissue will desirably achieve restoration. The granulation tissue rebuilds the majority of the gingiva in which fibers are arranged functionally in the direction of their tensile strength resulting in a functional scar. Epithelial cells migrate across the granulation tissue. In that the process of healing this type of wound involves a component of inflammation, along with need for new tissue ingrowth, which healing could be accelerated by use of NPWT as described herein.

When periodontal tissues have been damaged more profoundly to the level where the condition is considered periodontitis, the healing is often more complicated compared with simple gingivitis cases. Different cell types are required as compared to gingivitis cases, but elements of the process, including involvement of an inflammatory cascade, need for tissue regrowth and angiogenesis, often remain the same. The tissue repair process can likely be modulated by NPWT in a favorable manner. In the healing process, a desirable outcome of use of NPWT could be to allow the negative pressure environment, with the propensity to induce wound contraction, to encourage the re-formation of junctional epithelium (epithelium in contact with the base of the tooth, an important component of periodontal defense mechanism against infection) and periodontal ligament tissue.

Various embodiments disclosed herein incorporate features that can utilize various aspects of the oral anatomy to facilitate treatment of intraoral conditions, including the ability to distribute negative pressure and negative pressure effects to one or more areas within the oral cavity, including an equal and/or unequal application to a desired periodontal pocket and/or to various tissues surrounding an affected area. Improved oral treatment systems can optionally include various mechanical features in the oral appliance that could accomplish similar objectives, including the ability to equally distribute negative pressure to a desired area. In various embodiments, NPWT can be an effective adjunct in optimizing treatment for oral conditions like periodontal pocket formation, usually in conjunction with treatment and professional cleaning/debridement performed by an oral healthcare professional. Moreover, various oral wounds may heal faster with less scarring than wounds of the extremities and torso due to additional factors such as the presence of saliva, specific microflora of the oral cavity, and/or favorable physiologic properties (i.e., appropriate pH, higher concentration of lymphatic cells). Therefore, given the more rapid healing of gingival/periodontal tissues, NPWT can be an important adjunct in a treatment program.

FIG. 4A illustrates a partial cross-sectional views of a healthy tooth (i.e., an adult human molar) and associated gum tissue. In this embodiment, the tooth 100 can be separated into an upper crown layer 115 and a lower root layer 118. In the tooth, an exterior layer of enamel 122 surrounds an inner layer of dentin 130, which in turn surrounds an interior pulp layer 140 which contains various vascular and nerve networks. The gums or gingiva 160 surround the tooth 100, with an underlying layer of alveolar bone 170 deep to the gums 160 and root layer 118 of the tooth 100.

Figure 4B:
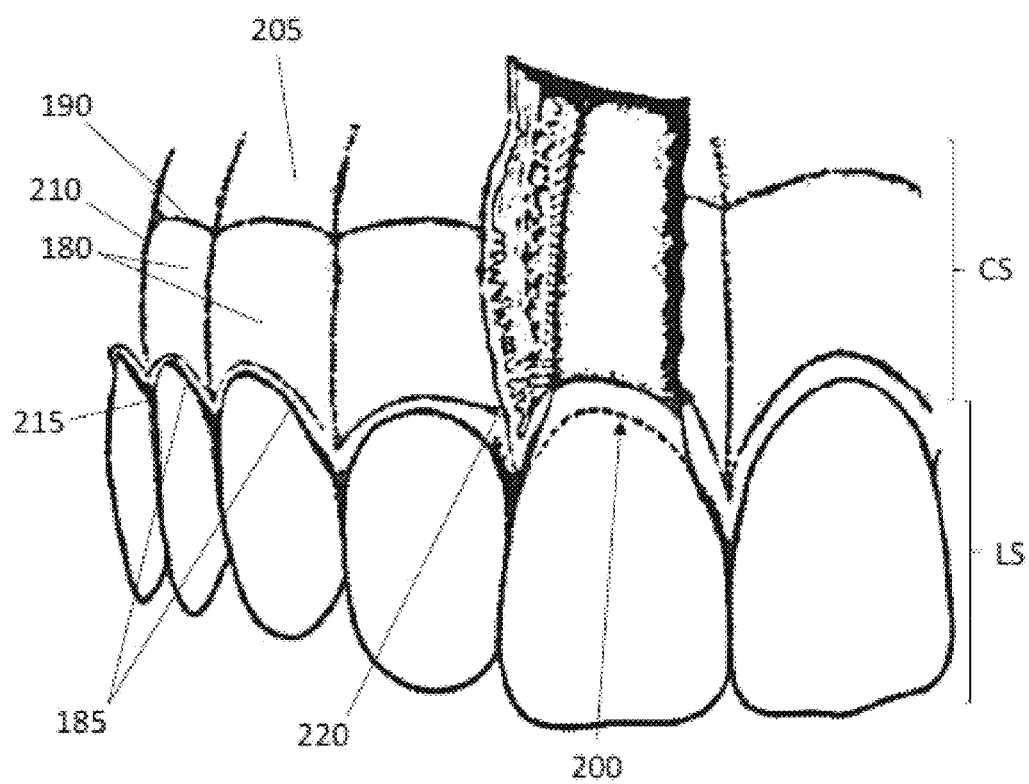
FIG. 4B depicts a magnified partial anterior view of various structures supporting the tooth base, including gingival tissues.
Figure 4C:
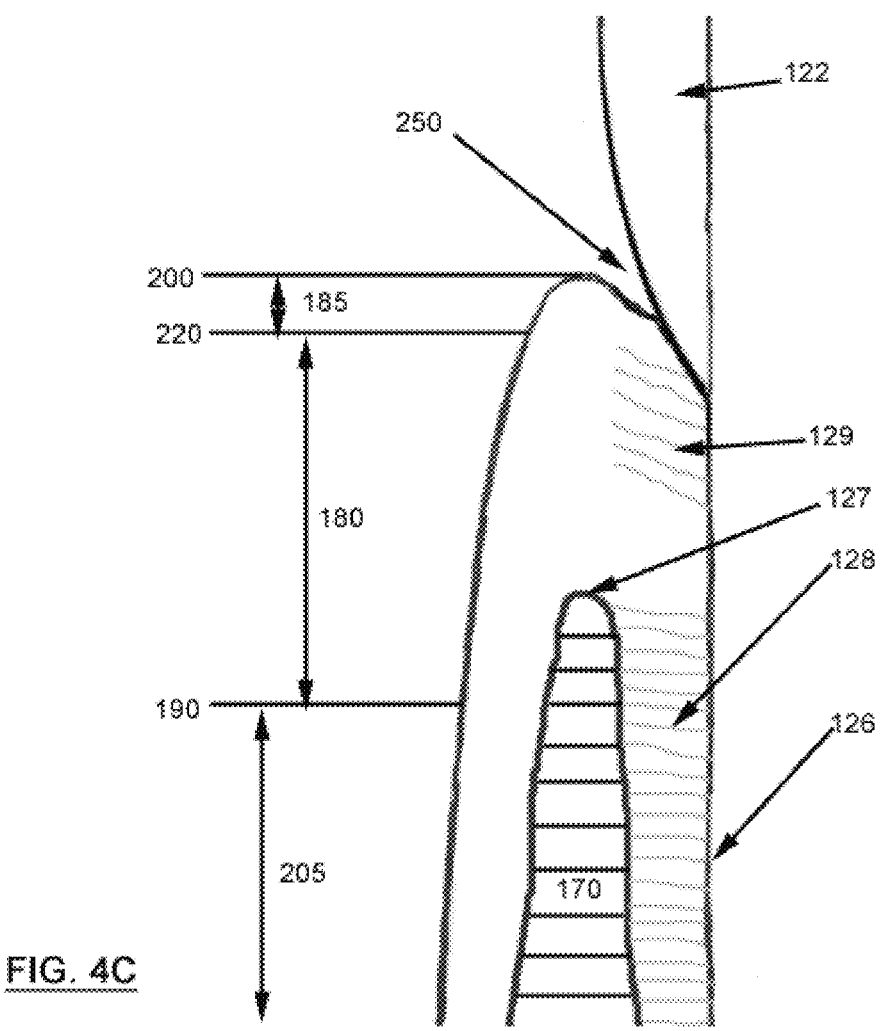
FIG. 4C illustrates a magnified partial cross-sectional schematic view of a healthy tooth and adjacent gum tissues.

As previously noted, the gum tissues 160 surrounding the tooth 100 in FIG. 4A appear relatively healthy, with little space between the gum tissue 160 and the root layer 118 of the tooth. As best seen in FIGS. 4B and 4C, the gums or gingiva are composed of an attached gingival portion 180 and an unattached gingival portion 185. The unattached gum tissue is referred to as the "free gingiva" or "marginal gingiva," which is the unattached portion of the gingiva that surrounds the tooth in a cuff-like manner. The unattached gum tissue fits closely around the tooth but is not directly attached to the tooth—which allows a dental professional to stretch the gum tissue away from the tooth surface using a periodontal probe to measure the depth of this space which, when it becomes deeper, is the periodontal pocket. The unattached gum tissue forms a minimal soft tissue wall within a gingival sulcus, where the unattached gum tissue meets the tooth in a thin rounded edge called the gingival margin 200 that follows the contours of the teeth. Also depicted is the alveolar mucosa 205, the mucogingival junction 190 (i.e., the upper edge), interdental grooves 210, interdental papilla 215 and the free gingival groove 220.

Figure 4D:
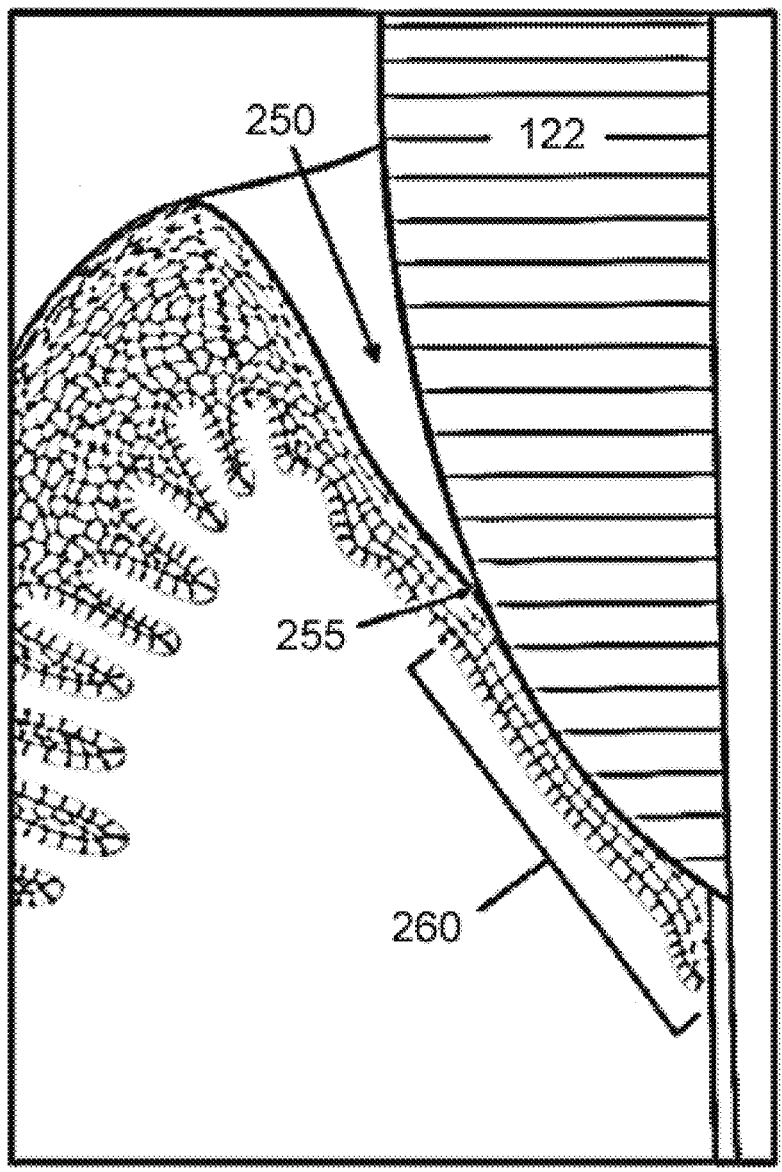
FIG. 4D illustrates a further magnified partial cross-sectional view of the healthy tooth and adjacent gum tissues of FIG. 4C.

FIGS. 4C and 4D depict various anatomical features in proximity to the gingival sulcus 250, which is the space between the unattached gums and the tooth surface. The gingival sulcus 250 in healthy individuals can be a V-shaped shallow space around the tooth, extending approximately 1-3 mm (i.e., a normal, healthy depth). At the base 255 of the sulcus is junctional epithelium 260, which is tissue that lines surface of the tooth enamel 122, where the attached portion gum or "attached gingiva" is attached to the root of the teeth. The junctional epithelium (shown in FIG. 4C at 129 and in FIG. 4D at 260) is a specialized type of epithelium that attaches to the tooth surface. Usually, the attached gingiva is tightly connected to the cementum 126 on the cervical third root and to the periosteum (connective tissue cover) of the alveolar bone 170—it lies between the free gingiva 185 and the alveolar mucosa 205 (i.e., alternatively it may lie between the free gingival groove to the mucogingival junction). The attached gingiva provides a variety of important functions, including withstanding mechanical forces from mastication, speaking and/or tooth brushing, and also prevents free gingiva from being pulled away from the tooth when tension is applied to the alveolar mucosa. The periodontal ligament 128 is a group of specialized connective tissue fibers that attach the tooth to the alveolar bone 170 within which it sits.

Figure 4E:
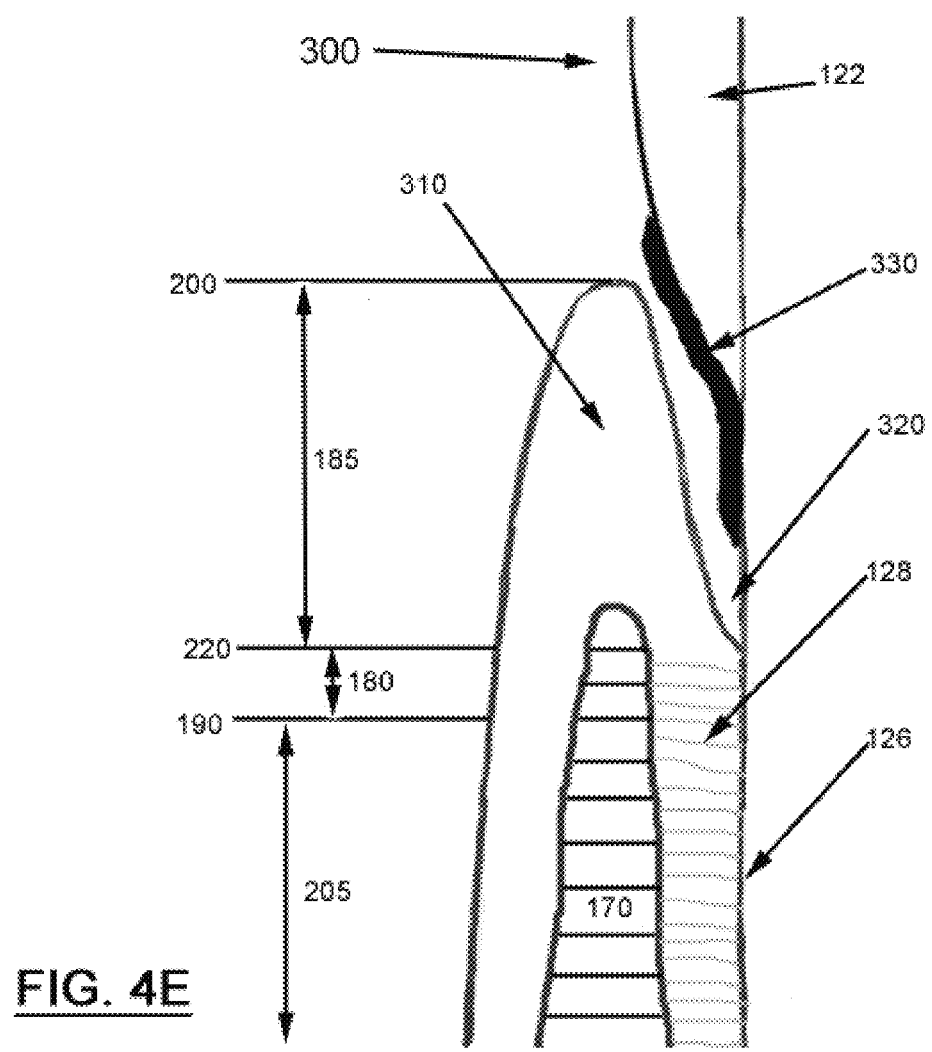
FIG. 4E illustrates a partial cross-sectional schematic view of one embodiment of a tooth and adjacent gum tissues suffering from periodontal disease.

The clinical picture of an exemplary tooth 300 affected by periodontitis is illustrated in FIG. 4E. As a result of chronic inflammation, the periodontal pockets can deepen with the pathologic anatomy illustrated in this schematic diagram. While the reasons for periodontal pocket formation are multifactorial, the basic process is characterized by a vicious cycle: the bacteria have a place to hide at the base of the pocket, essentially creating a situation of a chronic low grade infection. The reaction of the body to this process involves a cascade of events we know of as inflammation, and one of the sequelae of this chronic inflammation is that the tissue attachments become less adherent, and as a result there is further separation of soft tissues from the base of the tooth. The deeper the pocket becomes, the more difficult it is to clean, and the more inflammation occurs, thus continuing the cycle. To relate to FIG. 4E, the affected gingival tissues 310, as a result of this chronic inflammation, begin to detach from the surface of the tooth 300 and the enamel surface 122. The bacterial biofilm known as plaque 330 can extend to the base of the tooth and as the tissue attachments recede, to the cementum 126 which, with its irregular surface, provides even more places for bacterial plaque to exist. The depth of the pocket (from 200 to 320) can be measured by the dentist's periodontal probe, and once this distance is more than 3-4 mm, the pocket is difficult to clean even with aggressive home care. These periodontal pockets can be present chronically, as the opposing factors of healing and bacterial proliferation are at a standoff. Therefore, the need for an additional modality such as NPWT is illustrated by the fact that the natural history of periodontal pocket formation (especially untreated) is to worsen over time.

As the gingival sulcus 320 deepens, with resultant breakdown of the connective tissues and resorption of bone 170, there is less periodontal ligament tissue 128 to keep the teeth in place. The gingival sulcus can continue to deepen as the soft tissues and periodontal attachment fibers are destroyed, to depths sometimes reaching the alveolar mucosa. Recession (i.e., less gum tissue covering the base of the tooth, making the tooth appear longer) can occur, and along with destruction of the periodontium (the tissues that support and surround the teeth), including the bony tooth socket, with a potential for increased tooth mobility, which left untreated can result in tooth loss.

In various exemplary embodiments, an improved negative pressure dental system can comprise a custom oral appliance, a single or multi-lumen tube system, and a negative pressure generating device or machine. In various embodiments, the negative pressure dental system may include a variety of components, and various component arrangements and characteristics of the intra-oral environment can obviate any need for distributive foams, sponges and/or special dressings/fillers, which are typically used to equally distribute the negative pressure with vacuum and/or low pressure treatment of other anatomical regions such as the extremities.

In various disclosed embodiments, an oral appliance can be designed to interact with the oral mucosa, saliva and/or other anatomical structures in the mouth which, in combination with various mechanical structures and/or other features of the appliance, can provide a sufficient seal in order to maintain the application of negative pressure to the surfaces being treated. However, if desired, such supplemental tools such as sponges or special dressings or fillers could be incorporated into the various embodiments described herein.

As disclosed and described, the various embodiments may include oral appliances of having sufficient structural integrity to maintain a defined shape, but which are still desirably sufficiently flexible to create a sealed local environment (i.e., with the local moisture and/or various tissues) to effectuate a useful negative pressure environment. The negative pressure environment desirably facilitates egress of tissue fluids, reduction of edema (excess tissue fluid often associated with chronic inflammation) and due to the moist environment of the mouth, there is less risk of tissue dehydration/desiccation or cell death as compared to other areas in the body. Moreover, the oral mucosa is relatively well perfused, such that the added modality of the negative pressure environment can modify local conditions to promote healing and potentially close the space at various depths of the periodontal pocket.

Desirably, the disclosed systems and methods will bring healing cells into the depth of the periodontal pockets which are a physiologically disadvantaged area of the oral cavity. Just as this gradient can bring healing cells to cover an exposed bone in the extremities, the healing cells can help restore or reestablish the attached gingiva to the tooth surface with the formation of tissue that approximates long junctional epithelium, desirably providing a nearly normal gingival sulcus at the same healthy level.

In various embodiments, an improved negative pressure dental system or periodontal suction system may further comprise additional consumer-oriented features, such as (1) an appliance somewhat flexible for optimal patient comfort, yet which allows contact between the appliance and the gum surfaces; (2) an option for applying and/or modifying suction that is tolerable to the patient; (3) an appliance design that makes it easy for the patient to place and remove the appliance; and (4) an appliance design that is tolerable to wear for hours at a time, preferably including the opportunity to wear the appliance while sleeping.

In various embodiments, an oral appliance for use with the various systems and methods described herein may comprise an upper and/or lower custom oral appliance. The oral appliance may be formed via a direct impression from the patient's oral cavity (i.e., similar to boiling and forming a sports mouth guard), or a mold/impression of the patient's dentition may be taken, with the oral appliance formed from a dental cast (model of the patient's teeth) of the patient's dentition which is formed from that mold/impression. If desired, a dental professional or other individual can fabricate the appliance, which may include the step of augmenting the dental cast with periodontal dressing/filler at or proximate to the gingival sulcus on the model. In various embodiments, this periodontal dressing could be applied to the dental cast to help shape the appliance to allow for a channel to focus the negative pressure on the gingival sulcus (or on other areas in the mouth as indicated), but the periodontal dressing may also be applied in the patient's mouth at the time of the dental impression as another option for fabrication of the appliance.

Figure 5A:
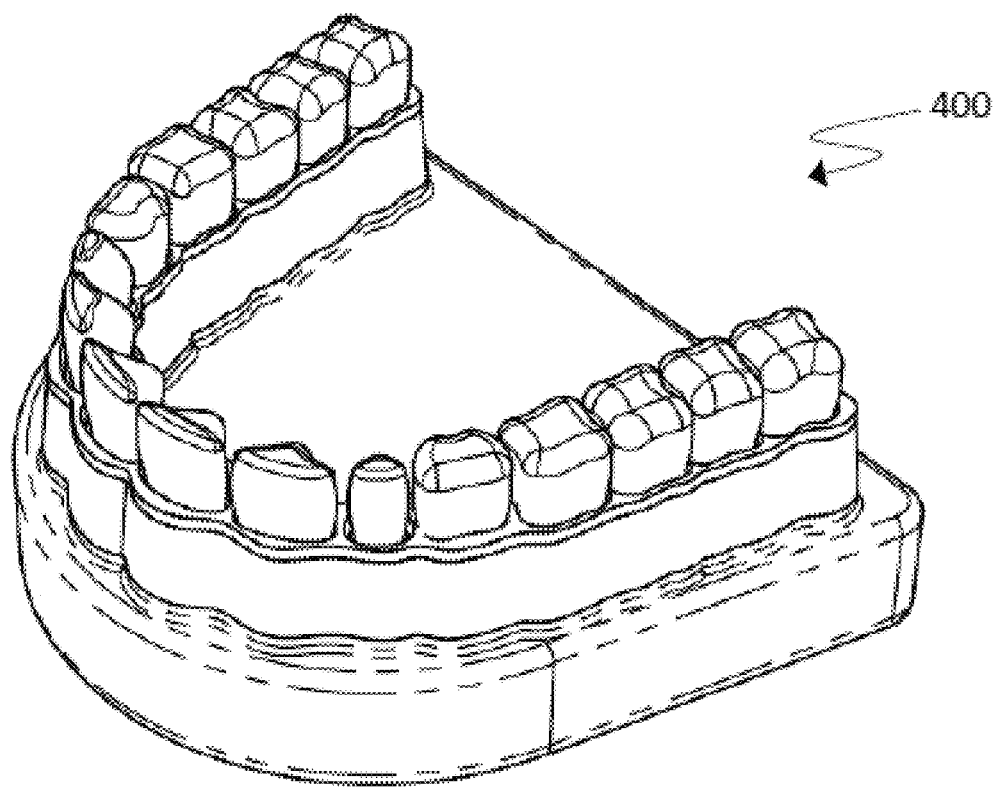
FIGS. 5A-5C depict various schematic views of a cast/model of a patient's dentition that could be utilized in forming an oral appliance.
Figure 5B:
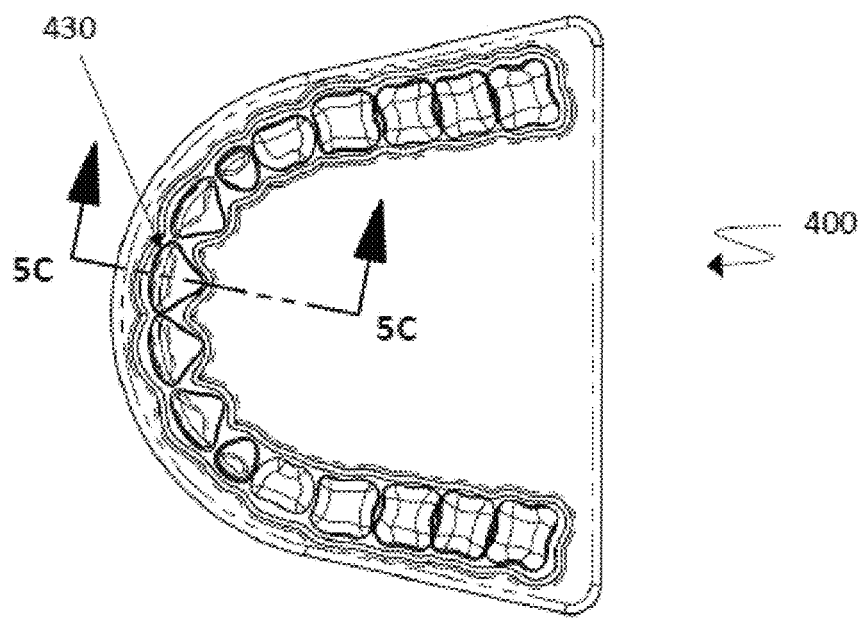
Figure 5C:
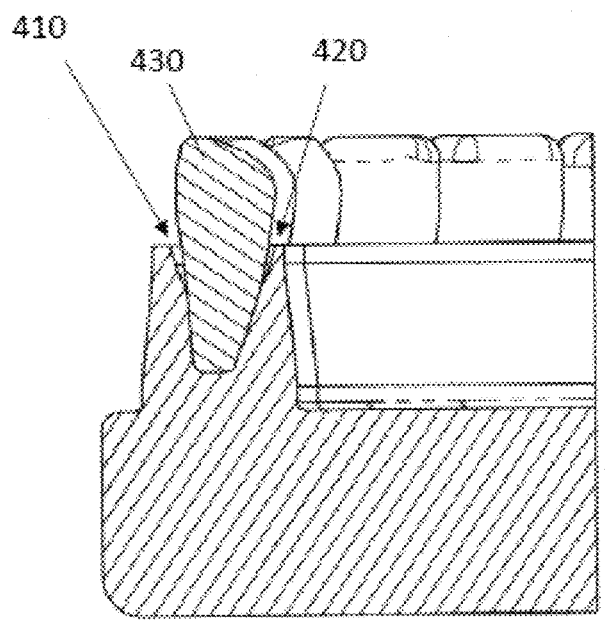

FIGS. 5A through 5C depict various schematic views of a cast of a patient's dentition 400, which could be utilized in forming an oral appliance for use in various of the embodiments described herein. As best seen in FIG. 5C, an anterior deep pocket 410 and a posterior deep pocket 420 have formed in gum tissues adjacent to a patient's right mandibular central incisor 430. In various embodiments, an augment (see in FIG. 6A at 450, and also referenced above as a "periodontal dressing") can be applied directly to the patient's dentition at the gum line (i.e., the gingival sulcus) prior to making the dental impression, or to the dental cast at the gingival sulcus for the process of fabricating the oral appliance.

Figure 6A:
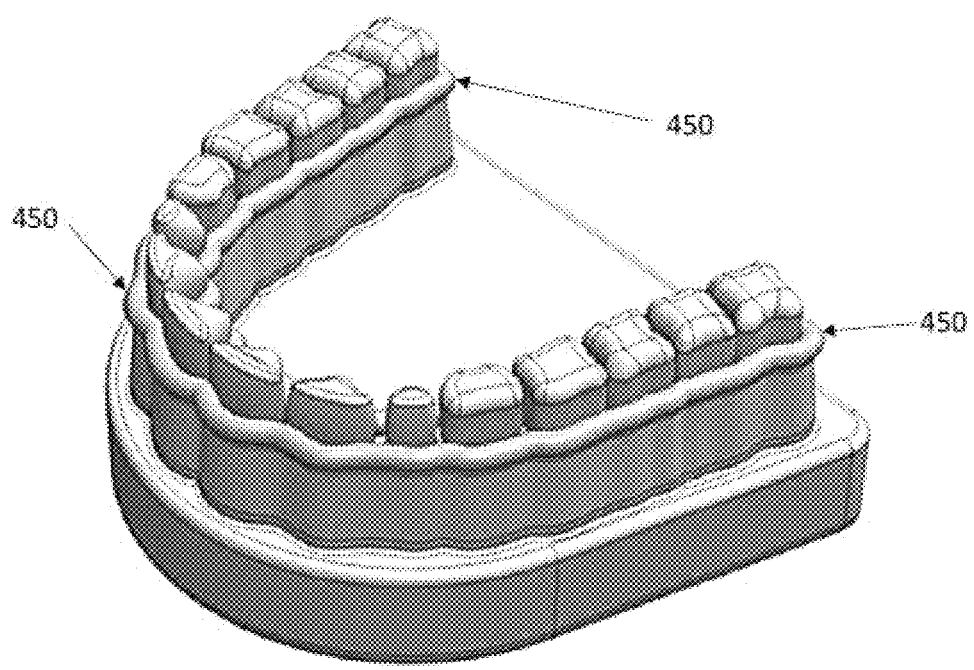
FIG. 6A depicts one embodiment of an augment that could be applied to the cast of the patient's dentition and/or gum line to help form the channel whereby the negative pressure would be applied.

While FIG. 6A depicts an augment extending completely around the tooth and/or gum line of the patient, it should be understood that other augments extending only along the front or back of the teeth structures, or even along one side of one or more teeth or any portion(s) thereof (i.e., along less than a single tooth width, or only between two teeth) are contemplated in various embodiments herein.

In various embodiments, the materials potentially used for the augment 450 could include those with moldable properties, such as the above mentioned periodontal dressing, or wax, and as noted, could be applied directly in the patient's mouth before impressions are taken, or could be applied to the dental cast prior to fabrication of the oral appliance.

Adding a periodontal dressing or other augment to at least a portion of a patients dentition and/or to a dental cast proximate at the gingival sulcus can create a "path" or channel proximate to the tooth/gum junction that can serve several functions: (1) the path or channel can provide a conduit within the oral appliance for the transfer and/or application of negative pressure to the gingival sulcus; (2) the path or channel can make the oral appliance easier to apply and remove, with less chance for the appliance to become wedged in any concavities of the patient's dentition; and/or (3) the path or channel can provide a conduit for the egress of tissue fluids, and if needed, gases, as they follow the negative pressure gradient, which could include waste metabolites and/or microbial flora removed by suction force. If desired, at least a portion of the channel and/or some portion of the oral appliance could contact one or more tooth surfaces, gum surfaces, palate surfaces, gingival surfaces, mucosal margin surfaces, the alveolar mucosa or even possibly the buccal mucosa. In various embodiments, the appliance can include one or more flexible and/or pliable surfaces or edges, which can desirably self-seal to adjacent anatomical structures without interfering with normal respiration of the patient through the nostrils and/or mouth. Desirably, through the combination of the flexibility of the appliance, and the ability to make an airtight and/or vacuum-tight seal (and/or partial seal thereof) at the areas where the appliance is in contact with some or all of the moist gingival surfaces and/or the tooth surfaces, the application of negative pressure to the concave surface of the appliance will desirably allow the appliance to be "compressed" or drawn towards the surface of the maxillary or mandibular dentition and/or gums (i.e., compressing the oral appliance using negative pressure to subject the oral wound and the oral appliance to a first pressure which is low enough to provide therapy to the oral wound and high enough to maintain a seal between the oral appliance and at least one of the members of the group consisting of the patient's dentition and a gum tissue of the patient), with the same mechanics as those that keep a suction cup on a wall. Since the teeth can act as a scaffold to provide for even distribution of the negative pressure, with this negative pressure distributed by the combination partly of the spaces between the teeth and partly due to the above mentioned channel that would focus pressure on the gingival sulcus, the appliance would likely not need any supplemental distribution devices, such as the sponge dressing that is required in wounds of the torso and the extremities. To illustrate with a simple example, if one thinks of a tent, the oral appliance could be the fabric of the tent, and the teeth (and/or portions of the appliance that contact the teeth) could be analogized as the tent poles. The space between the tent poles is analogous to the spaces between the teeth. If a fan were blowing air out of the tent, as long as the tent poles are holding up the tent, the tent will desirably not collapse under the reduced pressure. If desired, at least a portion of the channel and/or the oral appliance could contact one or more of the lingual surfaces (i.e., contacting the tongue), the buccal surfaces (i.e., contacting the inner aspect of the cheeks) and/or the labial surfaces (i.e., contacting the inner aspect of the lips) outside of the dentition, as well as other surfaces within the mouth.

Figure 6B:
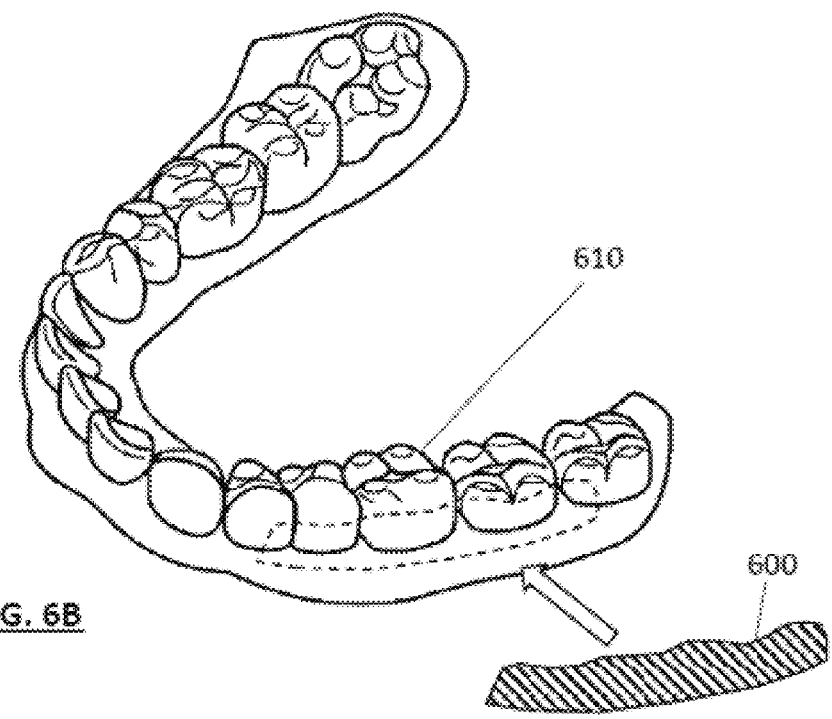
FIGS. 6B and 6C depict one alternative embodiment of an augment applied to the cast of the patient's dentition and/or gum line also to help form the channel whereby the negative pressure would be applied.
Figure 6C:
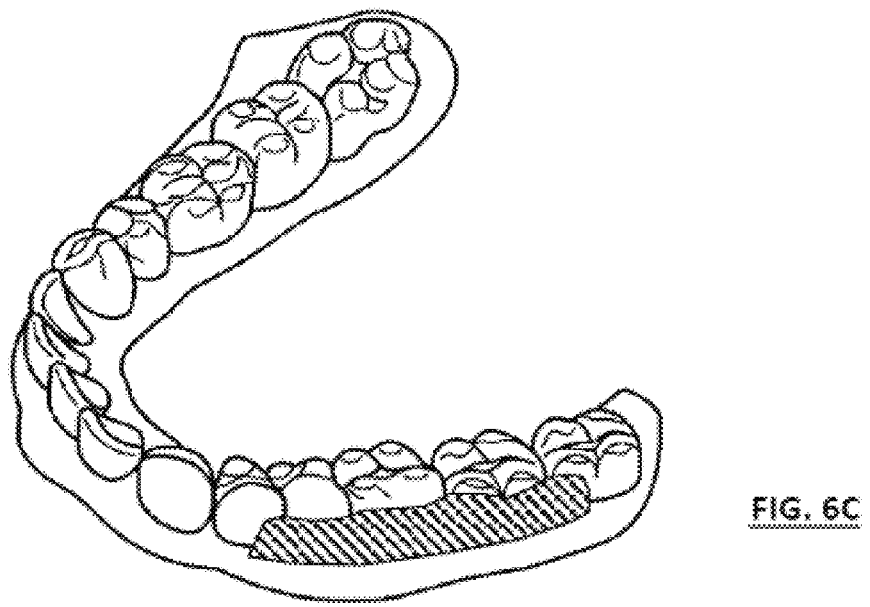

In one exemplary embodiment, such as shown in FIGS. 6B and 6C, a dental/periodontal dressing or augment 600 (or other material intended for forming the channel, including the augments previously described) may be placed on or adjacent to a tooth and/or gum structure 610 prior to making an impression of the patient's teeth. Alternatively, the dental professional may place a dental/periodontal dressing at or proximate to the gingival sulcus base on a patient's dental mold (cast model of the patient's teeth). Such periodontal dressings may include various types of materials, such as wax, clay or other commonly accepted periodontal dressings used in the industry (e.g., where the periodontal dressing composition may contain zinc oxide with eugenol, zinc oxide without eugenol, quaternary aluminum borate cement, cyanoacrylate, etc.). The periodontal dressings may be applied with a thickness and/or shape that desirably corresponds to a thickness and/or shape of the resulting channel, which in at least one exemplary embodiment comprises a thickness of 2-5 mm at or proximate to the base of the gingival sulcus, with a rounded or curved upper surface.

Figure 7:
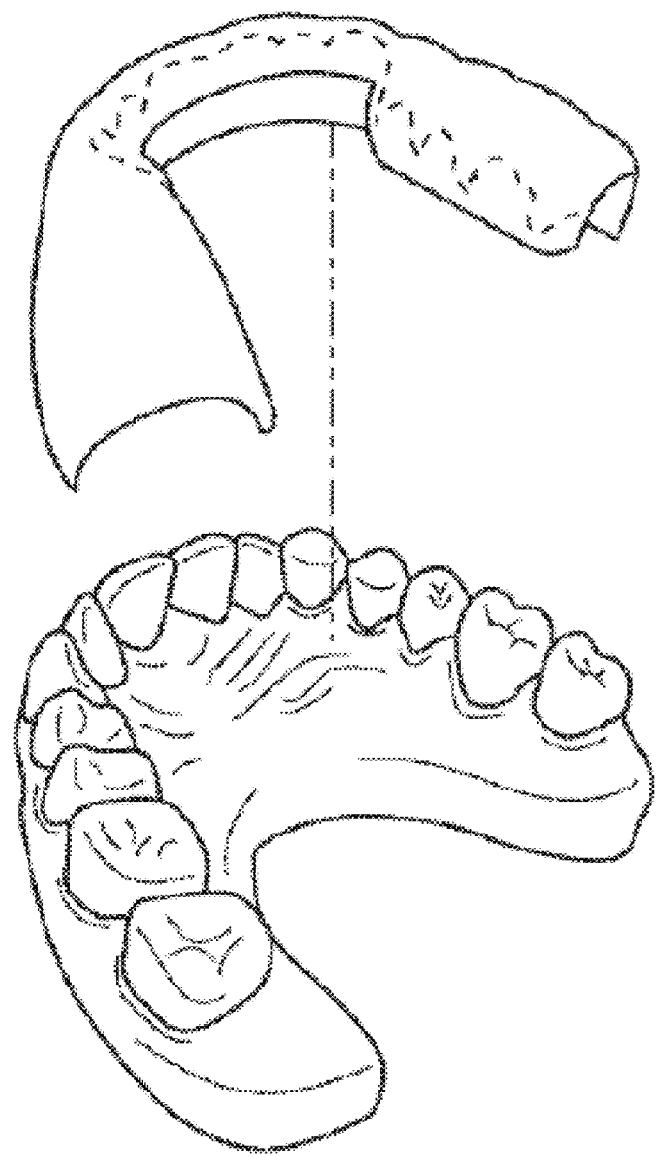
FIG. 7 depicts one exemplary embodiment of a dental impression tray containing a pliable impression material that can be placed over a region of interest of a patient's dentition.
Figure 9:
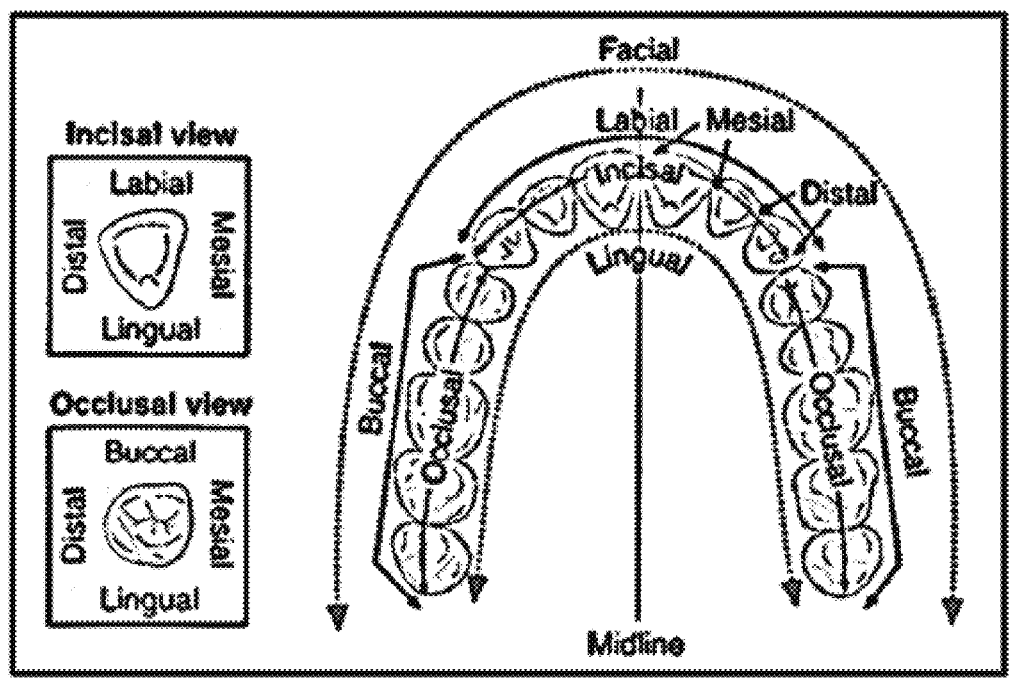
FIG. 9 depicts various anatomical references for typical tooth positions within an oral cavity.
Figure 10:
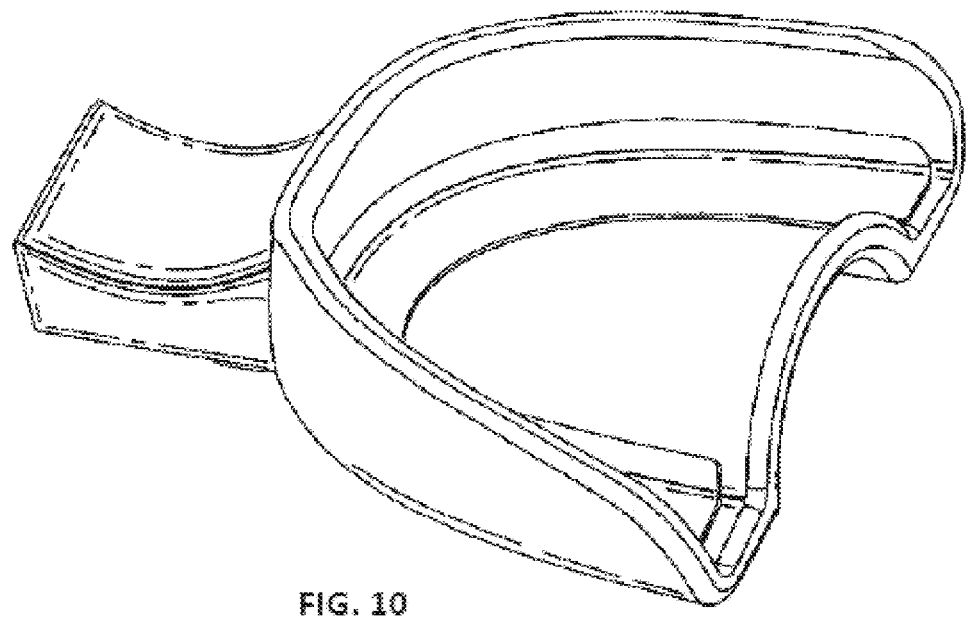
FIG. 10 depicts another alternative embodiment of a dental impression tray containing a pliable impression material that can be placed over a region of interest of a patient's dentition.
Figure 16:
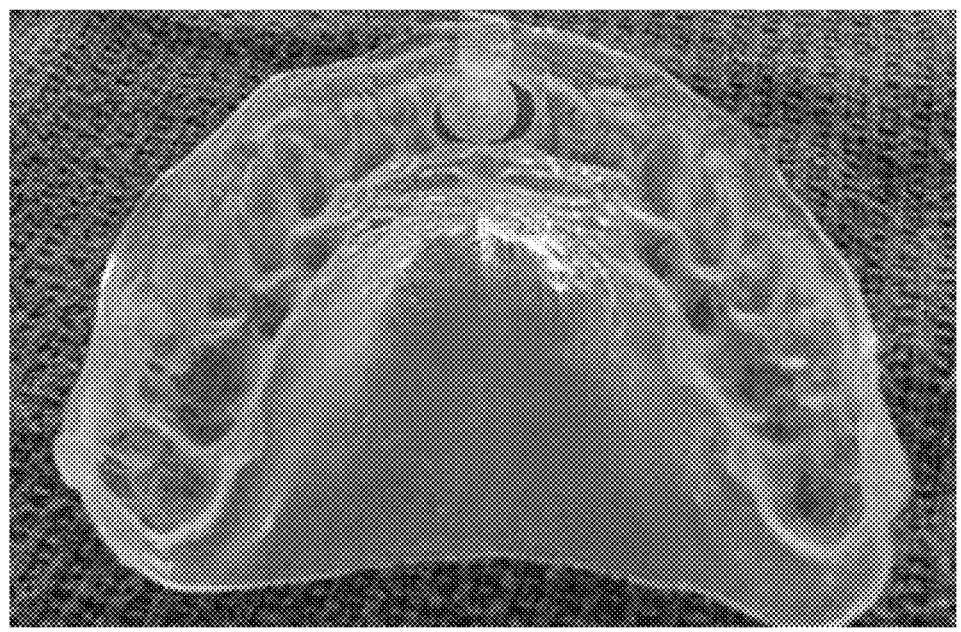
FIG. 16 depicts a view of one exemplary embodiment of a negative pressure oral appliance, including an upper arch prototype.

In other exemplary embodiments, a suitable oral appliance may be fabricated by a service provider such as a periodontist or by the patient's general dentist. A dental impression, which is a negative imprint of some or all of the hard and/or soft tissues in the mouth, can be utilized to make a positive impression, or dental cast. A series of one or more channels could be sculpted into the negative imprint (i.e., removal of impression material from the negative would desirably result in an intentional "void" in the oral appliance, such as one or more "channels"), or additional material could be added to the cast (i.e., addition of material to the dental cast would desirably result in an intentional "void" in the oral appliance). Impression materials could be designed to be a viscous liquid, a semi-solid, a solid material and/or a thixotropic material. If desired, a combination of two or more different impression materials could be used, or the same impression material having two different consistencies. Impression materials could be held by a container (i.e., a tray) designed to roughly fit over the dental arches, and quickly set to a solid (usually in a few minutes depending on the material), leaving an imprint of the structures of the mouth. If desired, a plurality of channels could be created, including two or more parallel channels proximate to similar gum tissues/dentition and/or two or more channels along different areas of the dentition within the same oral appliance.

Where a dental impression is taken, it would desirably capture a part or all of a patient's dentition and some or all of the surrounding structures of the oral cavity that are intended to be in contact with and/or adjacent to the negative pressure environment (see FIG. 7) and/or the oral appliance—one exemplary embodiment of a suitable appliance could include a palate contact surface, such as shown in FIG. 16. In one exemplary embodiment, the dental impression may include at least one or more surfaces within the oral cavity, including lingual, facial (i.e., labial or buccal), proximal (mesial, distal), occlusal and/or incisal ridge or edge (see FIG. 9). Various surrounding structures and/or tissues included in such an impression may further include at least one of the hard palate, the soft palate, the floor of the mouth, the gingiva (i.e., from all or some portion of the surface of the teeth to the mucosal margin) and/or the teeth.

Figure 8A:
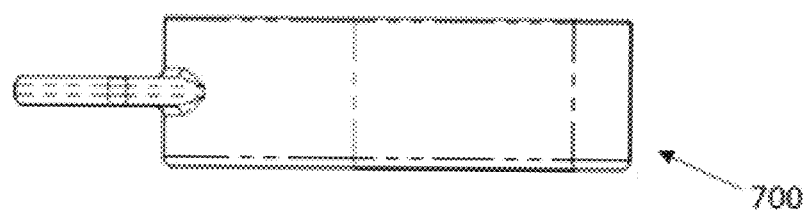
FIGS. 8A-8D depict various views of one alternative embodiment of a dental impression tray containing a pliable impression material that can be placed over a region of interest of a patient's dentition.
Figure 8B:
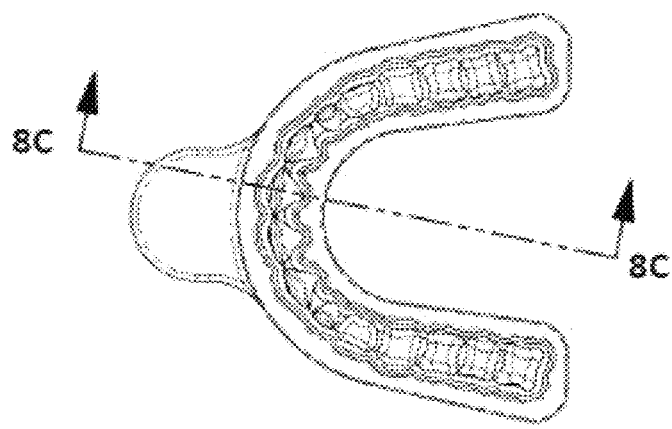
Figure 8C:
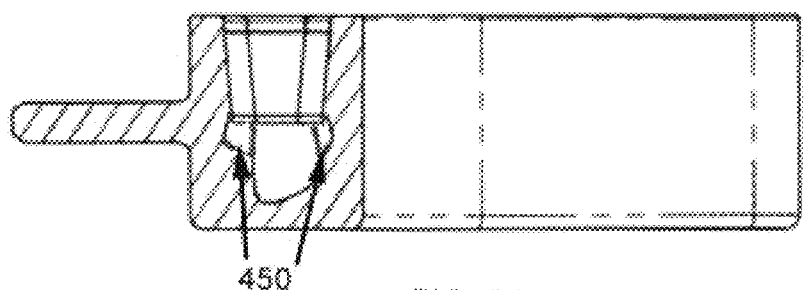
Figure 8D:
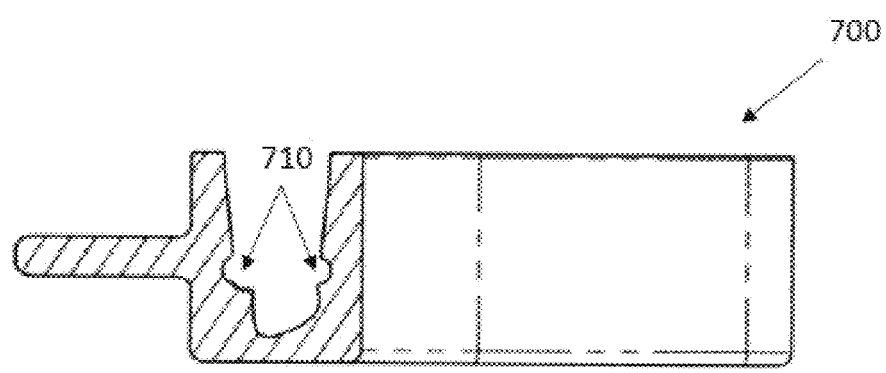

In various alternative embodiments, the patient may choose to complete an impression without professional dental assistance, with the impression performed by using a "home impression kit." The kit may include some viscous, thixotropic (or other type) material that can be introduced into the mouth via a stock dental impression tray (see FIGS. 8A through 8D and FIG. 10), where the patient may take an impression of their own teeth, wait for the impression to solidify, and forward (i.e., mail) the impression to a $3^{rd}$ party manufacturer to create the custom suction oral appliance (adding the additional material to the cast (see 450 of FIG. 8C) to create a channel for application of negative pressure (see 710 of FIG. 8D). Stock impression trays can be manufactured in various range of sizes and shapes, from which the closest size and/or shape tray can be selected that matches the dimensions of the dental arches (or portions thereof) of the person who is to receive the impression. Such stock trays may be manufactured from different types of materials that are commonly used in the industry (i.e., metals, elastomeric materials such as polysulfides, silicones, or polyethers and/or Plaster of Paris). Alternatively, a periodontist, dentist or other dental professional may take an in-office impression of a patient's teeth using a special or custom tray. The custom or special tray may be specialized to fit a specific patient's mouth, and may come equipped with a handle and/or other manipulation features for easy removal. The special or custom trays may be manufactured from any accepted materials commonly known in the industry, and is various embodiments would include materials and/or features to allow perforations, apertures, channels or other features to be created by drilling or other tools prior to the creation of the oral appliance.

In various additional embodiments, an oral appliance might be designed, manufactured and/or fitted to a patient utilizing non-invasive imaging data, which could include Panorex data, CT-Scan data (including dental cone beam CT scan), MRI scan data, X-ray data, ultrasound or sonogram data, laser scanning and/or other minimally invasive and/or non-invasive data. In other embodiments, visual depictions of the oral environment, including camera phone pictures (which might include sizing templates held within the field of view), might be uploaded to a website and utilized to create a 3D rendering of some or all of the oral cavity. Creation of the suitable oral appliance can include the computer aided design and/or manufacturing (including 3D printing or molding/machining or oral appliances) of patient specific and/or patient adapted features having various predefined shapes, sizes, widths, spans, thicknesses and/or contours based, at least partially, off of anatomical shape information obtained from one or more pre-operative scans.

FIGS. 8A through 8C depict exemplary methods of creating an oral appliance from a patient's dentition and/or from a dental cast thereof. As noted above, an augment or dental/periodontal dressing has been applied to the gingival sulcus (and/or other anatomy) of a patient's dentition or to a dental cast thereof (see also FIG. 6A, feature labeled 450), a dental impression tray 700 containing a pliable impression material can be placed over the dentition/cast and an impression made of the region of interest (see region 450 in FIG. 8C). Once the material within the impression tray 700 has hardened, the impression can be removed, with the impression comprising a negative image of the area of interest (see FIG. 8D), which in various embodiments can desirably include voids and/or channels 710 positioned proximate to the gingival sulcus and/or other locations proximate the teeth and/or soft tissues (which could correspond to the location and/or size of the augment or dental/periodontal dressing previously noted).

Desirably, the dental impression will result in an imprint (i.e., a 'negative' mold) of teeth and soft tissues, which can then be used to make a cast of the dentition. A cast of the dentition is a three-dimensional "positive" model of the patient's dentition (i.e., a patient's maxillary and mandibular arches), which may allow a dentist to determine the optimal locations for application of negative pressure treatment, treatment planning, patient education and development of the desired contact surface(s) required for treating the affected areas involved with periodontal pocket formation (see FIGS. 4A through 4E). In various embodiments, various features such as apertures, channels, sealing features and/or related shapes could be created by modifying the dental cast, by modifying the shape of patient's dentition, and/or by modifying the shape of the ultimate cast, formed or molded appliance. Such techniques could include applying a periodontal dressing to the region of the gingival sulcus on the dental cast prior to the creation of the oral appliance, and/or machining of the appliance to remove material in a desired manner (including the creation of channels and/or openings as described herein, or various combinations thereof). Various materials, methods and techniques known in the art may be used to create an appropriate anatomic model of the oral appliance, which can be customized as necessary for each patient's required treatment. For example, gypsum or plaster may be used to construct a cast, and similar materials having some degree of moldability (i.e., wax) could be used to modify the cast to direct, apply and/or concentrate negative pressure in a desired and/or appropriate manner.

In various embodiments, an oral appliance can desirably be fashioned from the impression tray 700 (FIG. 8D), with the associated channels 710. As best seen in FIGS. 11A through 11D, an oral appliance 800 for use with the present invention can include inner surfaces that abut the patient's teeth and gums that are configured to substantially match at least some portion of the patient's dentition, with at least one channel 720 (see FIG. 11D) proximate to the gingival sulcus.

Desirably, a source of negative pressure (i.e., a vacuum source) can be provided to the oral appliance, with the negative pressure transferred to the channel 710 for application to the patient's anatomy. In at least one exemplary embodiment, an oral appliance 800 (see FIG. 12) can include an attachment point 810 for one or more tubes (including multiple tubes, not shown), with the attachment point 810 including a lumen 820 which can connect to channel 710 on the inner surface of the appliance 800. Desirably, the attachment point 810 will be positioned on a frontal surface of the oral appliance 800, and would most desirably extend comfortably between the lips of the wearer when the appliance was in a desired position. If desired, the attachment point could include flattened outer surfaces to more comfortably fit between/against the lips of the wearer, although various other positions and mounting arrangements for the attachment point are contemplated herein. Moreover, alternative embodiments could incorporate the use of multiple tubes and attachment points, including multiple vacuum lines and/or a combination of supply and vacuum lines for the sequential and/or intermittent application of medicaments and vacuum, etc.

Figure 15A:
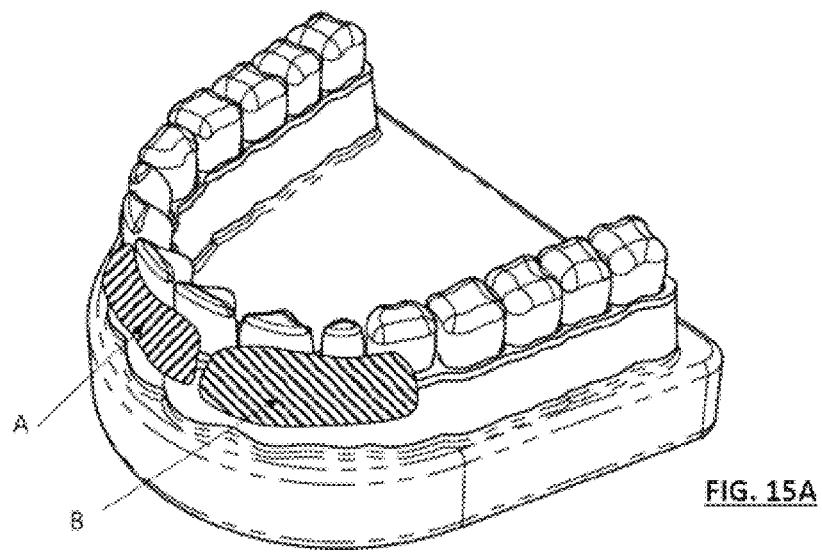
FIGS. 15A and 15B depict one alternative embodiment of an oral appliance incorporating a dual tubing and dual channel arrangement.
Figure 15B:
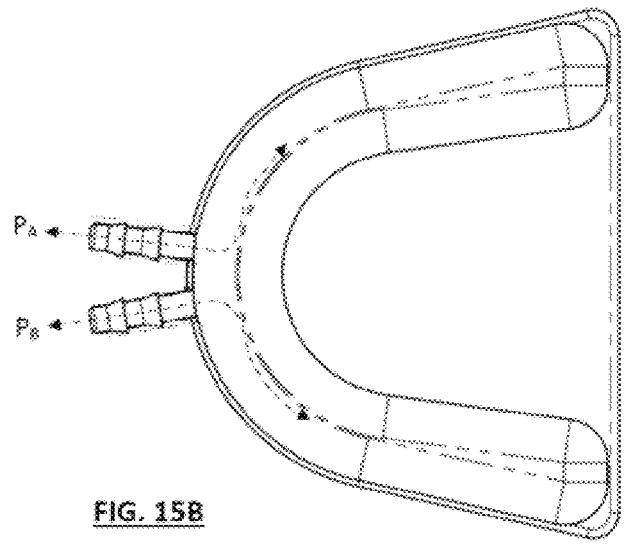

FIGS. 15A and 15B depict one embodiment of an oral appliance with a dual tubing arrangement that could be utilized by one exemplary method for retaining an oral appliance on a desired location of the patient's dentition during intermittent negative pressure therapy. In this embodiment, a first channel can be provided that applies a first amount of negative pressure $P_A$ to a first region A of the dentition, and a second channel can be provided that applies a second amount of negative pressure $P_B$ to a second region B of the dentition. If desired, the first and second negative pressures could be applied in an alternating fashion, with at least some portion of the oral appliance being "compressed" and/or drawn towards the relevant portion of the dentition at all times.

The oral appliance may be comprised of commonly available materials currently used in dental applications and also in the production of sport mouth guards (i.e., a semi-flexible plastic such as Ethylene Vinyl Copolymer, commercially available from Henry Schein, Inc. of Melville, N.Y., USA) which can be processed and shaped using standard vacuum forming processes known in the industry. If desired, vacuum forming techniques can facilitate modification of the shape of the oral appliance to accommodate a variety of attachment point types and/or designs for the suction and/or supply tubing. This suction tube may be fixed or may include a removable connection, and one of more tubes could be utilized for application of negative pressure and/or removal of tissue exudate.

If desired, one or more attachment points or adapters for the tubing might, to some degree, contact the front teeth and/or side teeth proximate to the mouth, with the lumen of the tubing desirably delivering negative pressure to the channel created along the gingival sulcus (which could include direct contact with the lumen and/or indirect contact with a lumen via the spaces between the teeth and/or via a lumen surrounding the back teeth of the appliance).

In various embodiments, negative pressure can be distributed to the gingival sulcus, which is the margin between the tooth and gum tissue but the channels could have different shapes and/or configurations, such as the various shapes illustrated in the schematic cross-sections of FIGS. 13A through 13F.

In various embodiments, an oral appliance could include patient adapted and/or patient specific features that correspond to some or all of a patient's upper dentition (and/or related soft tissues) and/or lower dentition (and/or related soft tissues). If desired, an upper dentition component and/or lower dentition component could comprise a non-clear polymeric or elastomeric material, such as a translucent blue or opaque tooth color, for example. The clear or opaque polymeric material may have additional properties, such as improved resistance to staining and/or color leaching. In addition, the polymer may not exhibit any odor or taste, yet still be substantially flexible and contain proper tensile and impact properties. The polymeric material may also be made clear or opaque.

In various embodiments, the oral appliance may be fashioned to focus a desired amount of negative pressure on a specific area of the patient's anatomy, which could include application to a partial upper dentition and/or a partial lower dentition (i.e., only a lateral or medial side of a tooth section and/or a portion of multiple teeth and/or a single tooth). In other embodiments, one or more channels in the oral appliance could be sized and/or arranged to apply a desired amount of negative pressure on a specific portion of the patient's gingiva and/or alveolar mucosa or to a region on the patient's palate. In various embodiments, the channels and oral appliance components could maintain sufficient structural integrity such that the channels desirably do not collapse (or do not collapse a significant amount) upon application of negative pressure, while in other embodiments a partial and/or complete collapse of the channels may be desired.

Figure 13A:
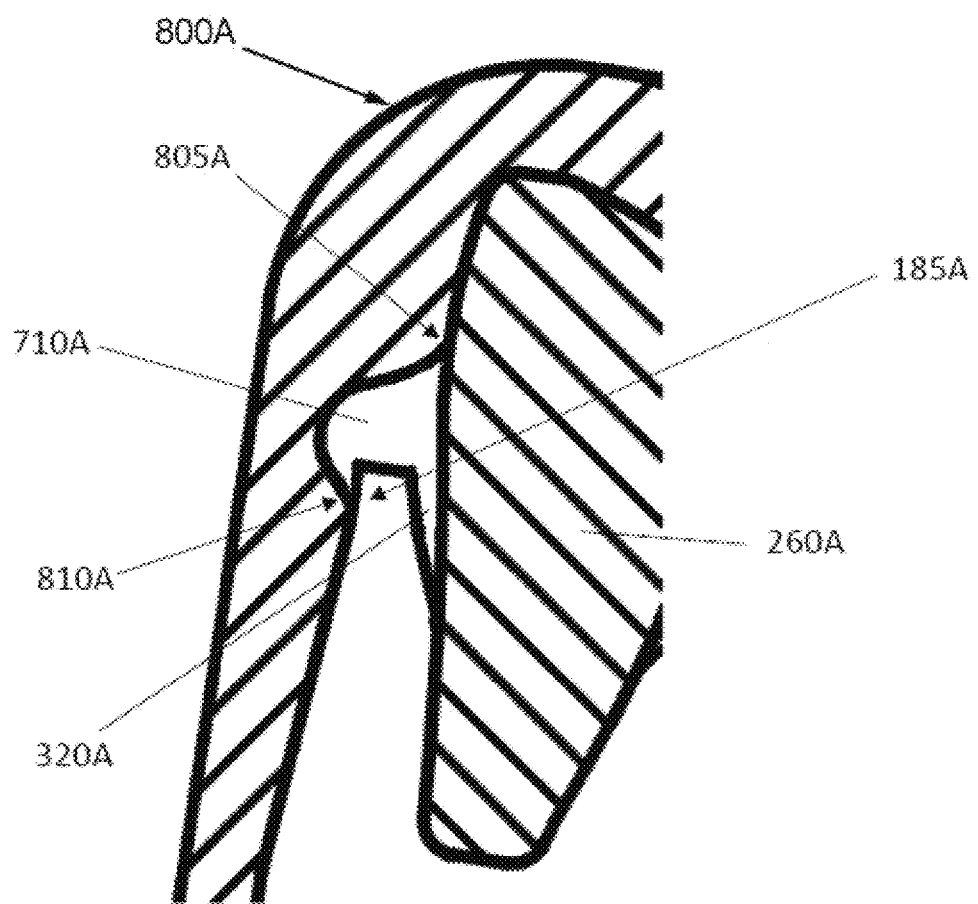
FIG. 13A depicts a partial cross-sectional schematic view of a channel of a negative pressure oral appliance and associated patient anatomy.

For example, in the embodiment of FIG. 13A, the channel 710A is desirably sized and arranged to apply negative pressure to a deep pocket area 320A of the patient's dentition, with a significant upper portion 805A of the appliance directly compressed against and contacting the tooth 260A. However, this negative pressure may also draw a lower surface portion 810A of the oral appliance 800A towards and into contact with a portion of the free gingiva 185A, which may push the free gingiva 185A into contact with the tooth 260A, potentially squeezing the free gingiva 185A between the appliance 800A and the tooth 260A potentially closing and blocking egress of tissue fluid from the deep pocket area 320A.

Figure 13B:
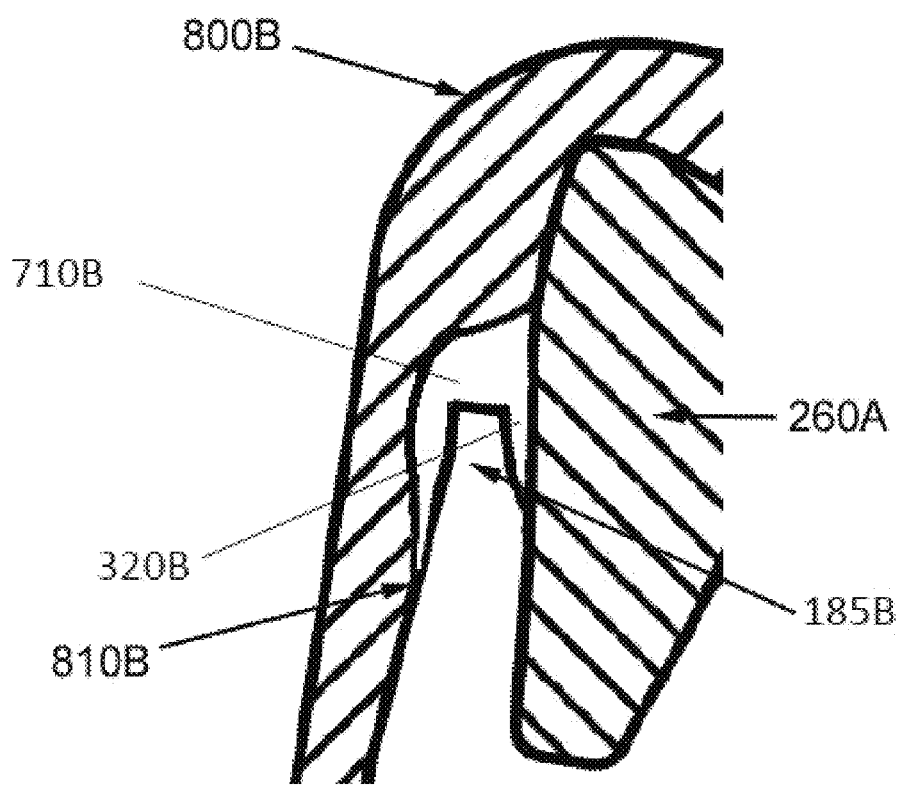
FIGS. 13B through 13F depict partial cross-sectional schematic views of alternative embodiments of negative pressure oral appliances incorporating various channel shapes and/or sizes, with associated patient anatomy.
Figure 13C:
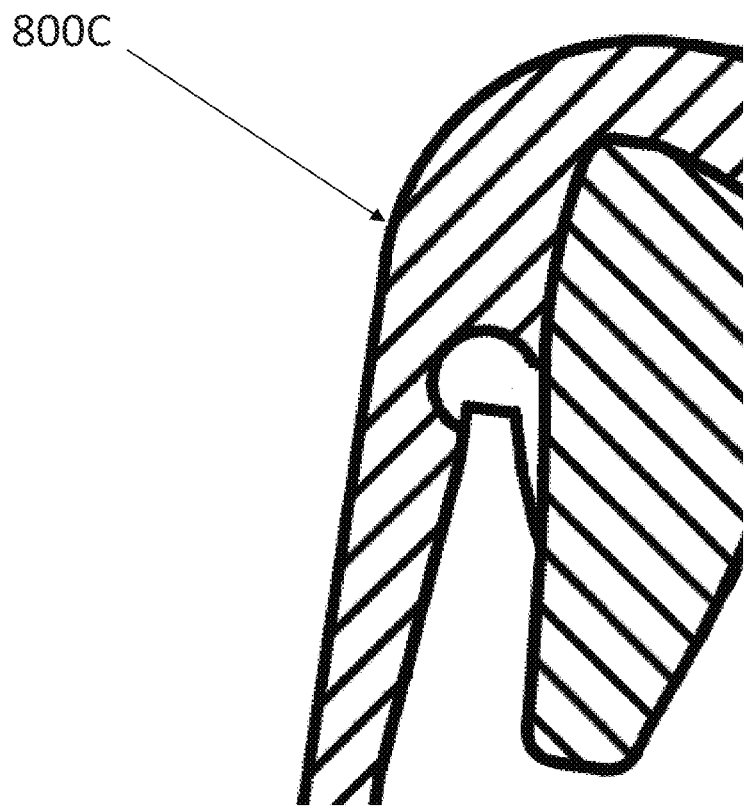
Figure 13D:
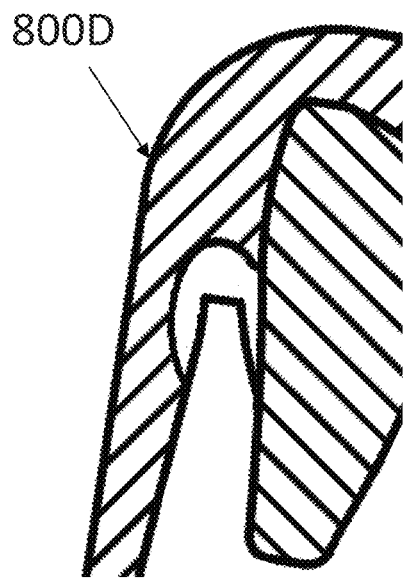
Figure 13E:
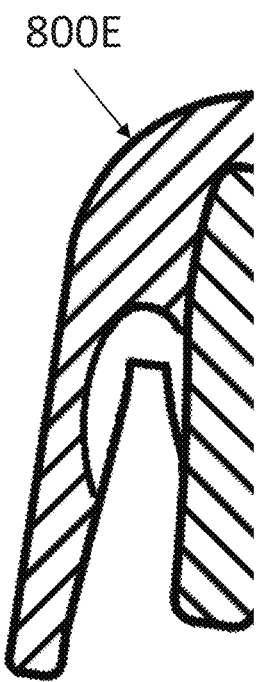
Figure 13F:
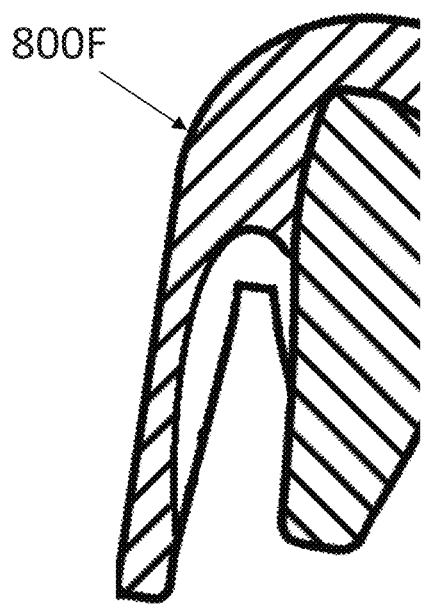

While pocket closure might be desirable in some situations, alternative channel designs may avoid the potential pocket closure as the negative pressure "compresses" the appliance and brings the surface of the appliance in contact with the gingival surfaces. For example, FIG. 13B depicts a channel 710B that is desirably sized and arranged to apply negative pressure to a deep pocket area 320B of the patient's dentition, wherein a lower surface portion 810B of the oral appliance 800B contacts the gingiva 185B below the deepest portion of the deep pocket area 320B, on the attached gingiva.

FIGS. 13C through 13F depict additional exemplary embodiments of channels of differing shape, size and/or design, including portions of the oral appliances (800C in FIG. 13C; 800D in FIG. 13D; 800E in FIG. 13E and 800F in FIG. 13F, respectively) that compress against and/or contact various surfaces of the patient's anatomy.

In various embodiments, an oral appliance can be fabricated to include one or more surfaces that directly contact and/or compress against various portions of the attached gingiva, as illustrated in FIG. 4B as CS (center section) of the patient's dentition. This attached gingiva is located somewhat distal from the teeth, and appliance contact with this surface desirably allows the appliance to contact gingival tissues beyond the gingival sulcus. By fabricating this appliance from the dental cast which near perfectly reflects the patient's individual anatomic morphology (in this exemplary embodiment), the appliance desirably conforms precisely to various hard and/or soft tissues of the patient's anatomy. The contact area is also illustrated by structure 180 in either FIG. 4C or 4E, allowing for appliance contact with healthier tissues and/or tissues having relatively more structural integrity than tissues affected by the periodontal pocket formation.

In yet another embodiment, an oral appliance could include an upper dentition component configured to be received on a patient's upper (maxillary) teeth, and formed to substantially conform to the contours of the patient's upper teeth, and upper dental arch, including the rear-most molars and some of the hard palate, such as the appliance depicted in FIG. 16. An exemplary upper dentition component may include an upper edge, a center section and a lower section, such as illustrated in FIG. 4B. The upper edge that may be configured as the edge that reaches a mucosal margin or the mucogingival junction of the patient (see 190 of FIG. 4B) which separates the attached gingiva 180 from the alveolar mucosa 205. The edge of the appliance, to accommodate this anatomical aspect, may include a wavy, scalloped shape/configuration (not shown) to desirably replicate a patient's mucogingival junction. In other embodiments, an oral appliance could include an upper dentition component configured to be received on a patient's upper (maxillary) teeth, and formed to substantially conform to the contours of the patient's upper teeth, and upper dental arch, including the rear-most molars. In certain embodiments, the upper edge could be configured such that the edge might reach and/or overlap at least a portion of a patient's attached gingiva.

In various embodiments, an oral appliance could include an upper dentition component, with one or more surfaces of the appliance desirably that could be in contact with an attached gingiva on surfaces adjacent to the cheeks (buccal) and lips (labial). This embodiment of an appliance could cover all of the dentition, if desired, and for the more central (lingual) area of gingival contact, sufficient contact area on the lingual gingiva tissue could seal the surface under the appliance compression to a sufficient degree to facilitate the transfer of negative pressure to a targeted anatomical region without displacement of the oral appliance and/or causing patient discomfort. Alternatively, an oral appliance may incorporate one or more surfaces in contact with the hard palate of a patient, which could provide sufficient appliance compression contact with the patient's tissues to seal the area under the appliance to a sufficient degree to facilitate the transfer of negative pressure to a targeted anatomical region without significant displacement of the oral appliance and/or causing patient discomfort. Additionally, contact of the appliance with the palate, which can be seen in the prototype orthosis of FIG. 16, could be advantageous in various embodiments since some of the strongest movements of the tongue are in apposition to the palate, and by allowing appliance contact with the palate, there is a decreased chance of involuntary tongue movements displacing the appliance and disrupting the seal (to maintain the suction/negative pressure). In various embodiments, the tongue may be in contact with lingual aspects of an oral appliance, which in various other embodiments could provide additional surface area for tissue contact. Where the compressed oral appliance can provide sufficient contact with various regions of the patient's anatomy (which may include the use of flexible and/or pliable materials in the oral appliance to contact such anatomy), there may be no need for supplemental sealing materials such as dental adhesives to create a sufficient seal. If desired, there may be variations in the materials used in parts of the oral appliance in contact with the arch, the dentition or the gingival sulcus region, possibly comprising a variety of different materials having differing properties (i.e., tensile strength, compression, flexibility, clarity, etc.), including the use of multiple materials of differing strength, compression and/or flexibility characteristics, including the use of a flexible ridge or tab of material to effect a desired seal at the periphery of the appliance, the gums and/or the dentition.

In various embodiments, an oral appliance may include a lower dentition component, which could be configured to be received on a patient's lower (mandibular) teeth, and this component could be formed to substantially conform to various contours of patient's lower teeth and/or the interior of the entire lower dental arch (floor of mouth), including behind the rearmost molars. The lower dentition component may substantially conform to the patient's anatomy. In a preferred embodiment, the appliance may also extend into and/or beyond the attached gingiva, since this region of tissue could desirably have more structural integrity than various other tissues affected by the periodontal pocket formation, as well as to create the suction seal, and also would desirably not be moved or loosened by random movements of the tongue.

Similar to the upper dentition component previously described, an oral appliance comprising a lower dentition component could include one or more surfaces to contact and compress against the dentition LS (FIG. 4B) of the patient and the attached gingiva CS. If desired, the margin of the appliance could be modified to reflect the wavy, scalloped configuration of the patients mucogingival junction 190 to replicate this aspect of the patient's anatomy. The appliance in certain embodiments could have contact with either attached gingiva 180 or alveolar mucosa 205 at the lower edge. Similar to the upper dentition appliance, the lower dentition component could also be fabricated with a channel created by applying a periodontal dressing to the gingival sulcus on the dental cast to create an oral appliance that focuses the negative pressure on the gingival sulcus. If desired, the outermost edge of the appliance may comprise a flexible material to promote the gingival contact necessary to compress the appliance and maintain the negative pressure environment between the appliance and the underlying tissues during vacuum application.

In various embodiments, an oral appliance comprising a lower dentition component could similarly cover all of the patient's lower dentition, including posterior to the back molars, with contact on gingival surfaces, which could allow the appliance to exploit the natural moisture of the gingival surfaces to create a seal for transfer of the negative pressure environment to the deep pockets. The lower dentition component may include one or more surfaces that contact an attached gingiva. The lower dental arch portion may extend as deep as possible, desirably without impinging on the soft tissues to avoid causing patient discomfort. As similarly described above for the upper component, the appliance may be comprised of materials with different properties, (i.e., tensile strength, compression, flexibility, clarity, etc.).

In various embodiments, an oral appliance can be fabricated to include one or more surfaces that directly contact various portions of the "center section" CS of the patient's dentition (see FIG. 4B), which are areas located somewhat distal from the teeth (wherein the appliance contacts additional gum tissues beyond the gingival sulcus). This appliance would desirably substantially conform to various hard and/or soft tissues of the patient's anatomy, and in a preferred embodiment the appliance could extend up to and/or beyond the "attached gingiva" (which could include contact with healthier tissues and/or tissues having relatively more structural integrity than tissues affected by the periodontal pocket formation.

While pocket closure might be desirable in some situations, other arrangements and/or alternative channel designs may provide for various other desired treatments of the patient's condition. For example, a channel could be desirably sized and/or arranged to apply negative pressure to a deep pocket area of the patient's dentition, wherein a lower surface portion of the oral appliance compresses against and/or contacts the gingiva at or near the deepest portion of the deep pocket area. Other embodiments could include a channel that is desirably sized and arranged to apply negative pressure to a deep pocket area of the patient's dentition, wherein a lower surface portion of the oral appliance is compressed against and/or contacts the gingiva at a location below the deepest portion of the deep pocket area. Still other embodiments could incorporate a channel that is desirably sized and arranged to apply negative pressure to a deep pocket area of the patient's dentition, wherein a lower surface portion of the oral appliance is compressed against and/or contacts the alveolar mucosa at a location that may be at or below a root of the tooth. If desired, a channel of varying sizes, shapes and/or locations could be created, with some or all of the channel wall(s) following, mimicking or approximating the individual depth of pockets proximate to each tooth.

In various embodiments, an oral appliance could include various features that (1) assist with equal and/or controlled distribution of negative pressure to targeted anatomical areas, (2) may provide a pathway and gradient for removal of tissue exudate, and (3) allow for ease of application and removal of the appliance. The oral appliance may optionally include one or more surfaces in contact with the tongue (lingual) and/or surfaces that contact the inner aspect of the cheeks (buccal) and lips (labial).

A wide variety of path or channel features can be provided on an oral appliance, including a plurality of channels that may or may not communicate with each other. Channel features may extend along the patient's entire upper and/or lower dentition, or along various portions thereof. If desired, at least a portion of the lingual, labial and/or buccal surfaces of the upper and/or lower dentition may include at least a portion of a path or channel (not shown) that may extend from occlusal to incisal to occlusal teeth, including along the complete perimeter of the teeth. Alternatively, the path or channel may be focused on a specific region or diseased area, where the path or channel may extend along only a portion of the teeth from the incisal to occlusal teeth. In addition, the width, depth and/or other shape features of the channel may alter along a portion of the teeth, which could include wider or shallower channel regions proximate to more diseased regions, and thinner channels proximate to more healthy tissues.

In one exemplary embodiment, a recessed path or channel could desirably be located at the level of the gingival sulcus and/or the free gingival groove of a healthy patient's gingiva. The diameter or width of the path or channel may be configured to extend proximate to the gingival margin and proximate to the free gingival groove of both upper and/or lower dentition components. This diameter or width may be approximately 1-5 mm for a healthy patient, or the dimensions of the channel for treatment of more diseased patients might have one component parallel (channel width) and one component perpendicular to the gum tissue (channel depth), with either dimension in the range of 1 to 5 mm (or more). A channel may include various configurations (i.e., rounded, squared, triangular, hemispherical, fusiform, elliptical, etc.). In addition, the configuration of a channel may be manufactured by removing material from the wall thickness of the oral appliance, or the channel dimensions may extend outwardly (i.e., bulge outward) while maintaining a consistent wall thickness.

Figure 11A:
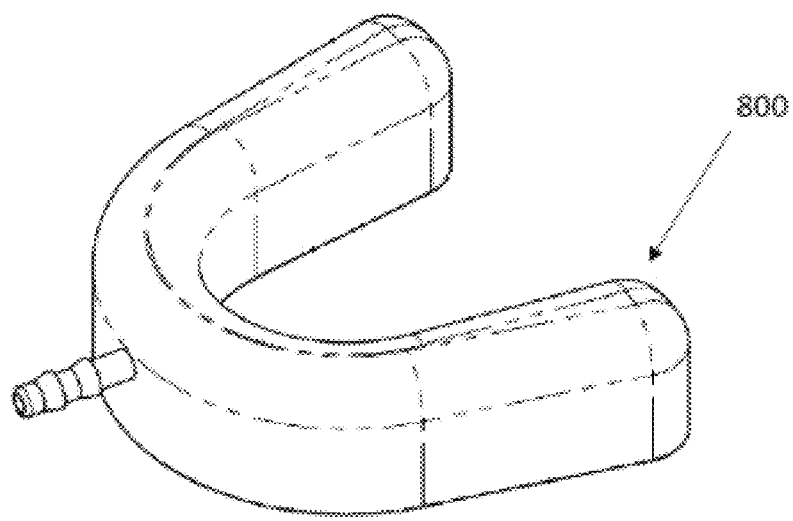
FIGS. 11A-11D depict one exemplary embodiment of an oral appliance for use in negative pressure oral therapy.
Figure 11B:
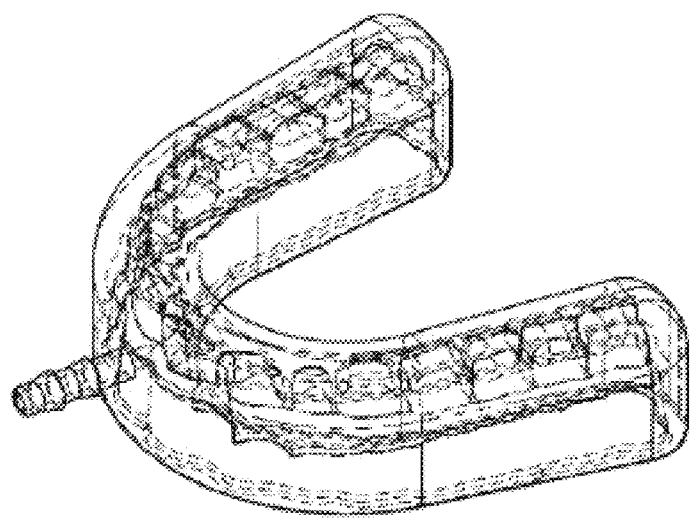
Figure 11C:
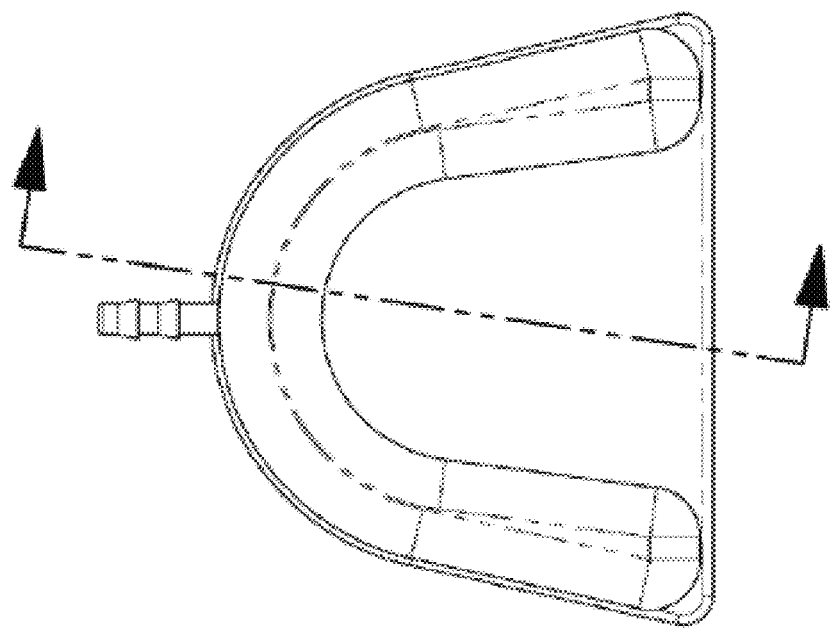
Figure 11D:
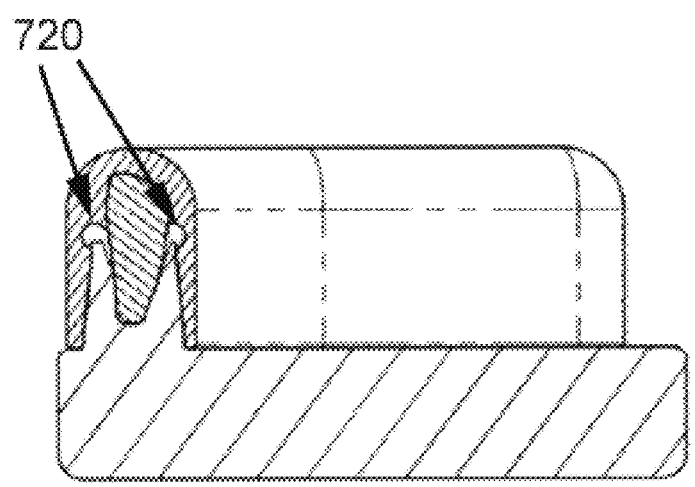
Figure 12:
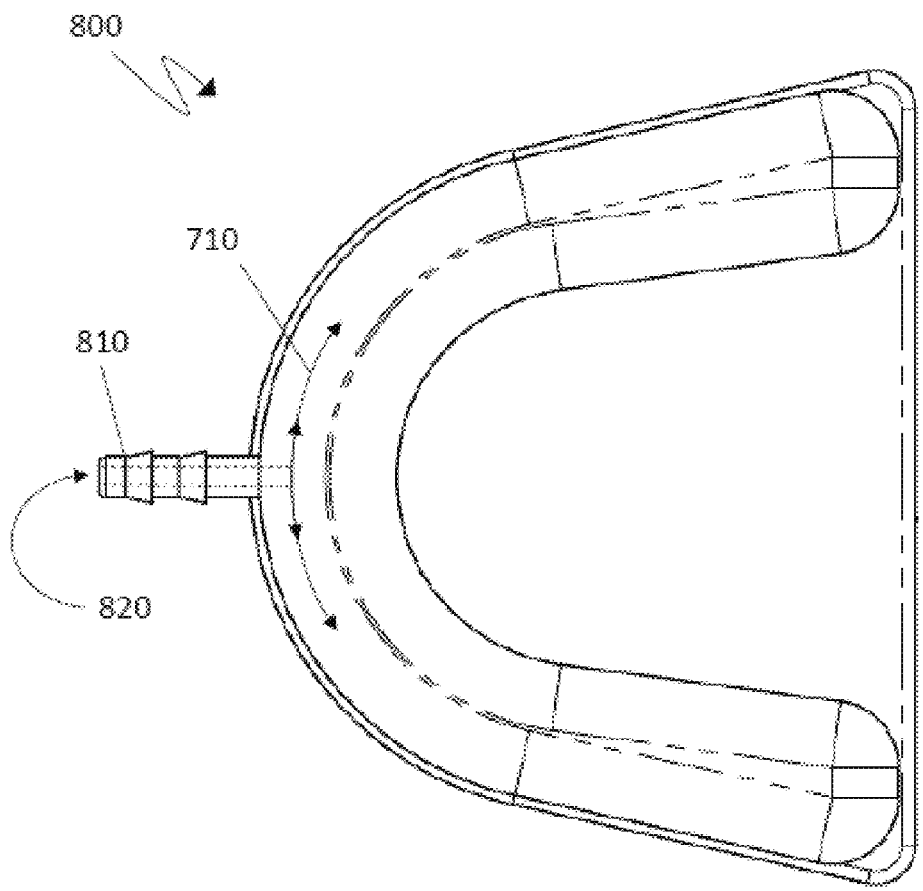
FIG. 12 depicts one exemplary pressure distribution path for negative pressure in the embodiment of FIG. 11A.

As best seen in FIGS. 11A, 11B and FIG. 12, an attachment point or aperture 810 (FIG. 12) can be provided on the oral appliance, with the disclosed aperture desirably positioned midline of the patient's mouth for comfort. In other embodiments, the aperture may be positioned anywhere along a front surface (i.e., the anterior aspect) of the appliance. The aperture may be sized and configured to fit within the recessed channel or path of the appliance, and the aperture could be slightly to the right or left depending on patient anatomy or patient preference, but its location would most desirably be limited by the margins of the lips (although other attachment points distal from the mouth are contemplated herein). Alternatively, a raised surface, additional cavity and/or additional space can be created at front of the upper and/or lower dentition component, including designs that facilitate the attachment of the negative pressure suction tubing to the appliance in a manner to reduce and/or eliminate the opportunity for bending stresses on the teeth, for eliminating inadvertent causation of patient discomfort, and/or for preventing possible tooth fracture if excessive bending forces were applied.

If desired, various embodiments could incorporate an antibiotic gel or similar medicament, which could be impregnated into the oral appliance. For example, if an antibiotic gel was delivered through the channel to a diseased anatomy (i.e., during a "pressurized" phase where gel is "pushed" into the appliance and/or during a "relaxation" phase where pressure is increased proximate to atmospheric pressures), the antibiotic gel may enter the periodontal pocket, and possibly migrate to a bottom of the pocket. Such motion of the gel might be further facilitated by intermittent "pulsing" of vacuum and pressure, which could help flush out unwanted fluids and/or materials while concurrently delivering a medicament treatment. If desired, the antibiotic gel composition might be of a sufficiently thick consistency such that it would not easily be extruded by the elasticity of the gingival tissue, and not washed away by saliva, nor extruded by the mechanical forces applied to the gums by normal mouth movements and eating/chewing. Aside from potential delivery of an antibiotic gel, since the appliance would desirably be in close apposition to the teeth and gingival tissue, the appliance could also concentrate other locally applied medications/treatments to these tissues, including whitening agents for the teeth, fluoride, and/or other medications as indicated. These medications/treatments could be formulated to have adequate viscosity so that they were not sucked into the lumen, but remained adjacent to the tissues being treated, kept in place by the negative pressure environment securing the appliance. In various embodiments, a medicament may be applied to the dentition and/or gums during a low pressure or appliance "compression" phase, which may then potentially be drawn into the periodontal pocket by the natural relaxation of tissues during a higher pressure or appliance "decompression" phase (i.e., when pressure in the appliance is increased and/or released to the surrounding atmospheric pressure and the tissues "rebound").

In various embodiments, a tubular adapter or other attachment could be connected to the aperture, which could be connected to a source of negative pressure. The tubular adapter could be virtually any commercially available adapter, or it may be a custom fashioned adapter configured as a transition to a multi-lumen tube system. In another embodiment, a multi-lumen tube system may include an oral appliance tube connection/aperture, a multi-lumen tube, a transition tube, transition adaptor, a tube clip, and/or a negative pressure tube adapter.

Figure 14:
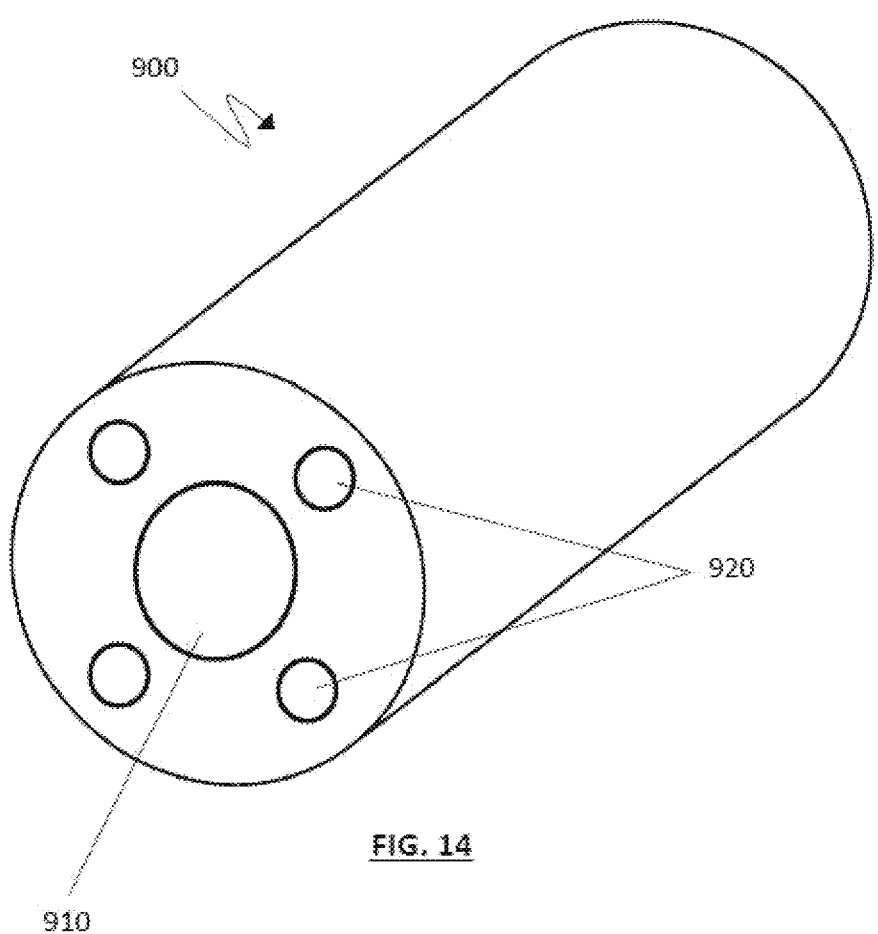
FIG. 14 depicts a cross-sectional perspective view of one embodiment of a multi-lumen tube.

As best seen in FIG. 14, a multi-lumen tube 900 (or suction tube) connected to the oral appliance may include one or more lumens 910 for extracting tissue fluid/tissue exudate, along with auxiliary channels 920 for measuring pressure (i.e., a pressure transducer), in a manner similar to pressure monitoring features currently incorporated into the Wound VAC system offered by Acelity/KCl. In various alternative embodiments, however, the need to incorporate a pressure transducer capability in the orthosis and/or other system components may be less compelling. Since the mouth is typically very sensitive, the patient could potentially tell if there were a significant loss of suction, as the appliance would desirably feel loose and would potentially displace. If desired, the upper limit of applied negative pressure could be controlled by the unit applying the negative pressure, or directly by the user, or might include a pressure relief valve somewhere in the appliance, the tubing and/or the vacuum pump.

Unlike standard negative pressure therapies employed in the extremities and/or torso (which often require constant pressure assessment and/or monitoring because blood in the lumen can clot (potentially reducing and/or negating the effects of treatment), such constant monitoring may not be necessary in an oral application because the fluid passing through the tubing in the current proposed invention may only comprise saliva and/other materials which do not clot (or which do not "clot" or otherwise harden to a significant level). If there were some obstruction of the tubing, as noted herein, the negative pressure from the vacuum source would likely reduce and/or disappear within the channel(s) of the oral appliance, causing the appliance to "decompress" some varying degree and/or become easily dislodged and/or malpositioned. However, if this appliance were used to help augment healing in a traumatic injury with potential bloody drainage, pressure monitoring could be an important optional additional feature. With regard to the configuration of the tubing, it may be cylindrical or may be a flat, multi-lumen tube (not shown).

In one exemplary embodiment, a diameter of one exemplary multi-lumen tube could be 7 mm or less, or optimally might be a custom size to fit a patient's mouth. The weight of the tube, the forces delivered by the lever arm/bending forces on the tube adapter, and/or the size and shape of a patient's mouth should be considerations for the size and configuration of the method of attachment of the tube to the appliance. The dentist may have various sizes and configurations available to provide a specialized fitting.

In addition, the single (optimal) or multi-lumen tube may be flexible, but desirably rigid enough to withstand continuous or intermittent negative pressures in the ranges of 25-250 mmHg without significant collapse. Intermittent negative pressure can include compressing the oral appliance using negative pressure to subject the oral wound and the oral appliance to a first pressure which is low enough to provide therapy to the oral wound and high enough to maintain a seal between the oral appliance and at least one of the members of the group consisting of the patient's dentition and a gum tissue of the patient, and decompressing the oral appliance to a second pressure above the first pressure sufficient to maintain the oral appliance in a desired position on the patient's dentition while relaxing compression about the oral wound. Furthermore, since patient comfort may be paramount (i.e., patients typically fail to comply with treatments that are not tolerable), designs that allow the patient to tolerate wearing the oral appliance for several hours at a time, usually overnight while sleeping, are desirous.

The oral appliance may include a tube adapter that could transition from a single to multi-lumen tube to allow for both the extraction of fluids, supply of medicaments and/or, if desired, monitoring of pressure. Commercially available single lumen drain tubes which are able to resist suction forces are soft and flexible, as small as 6-7 mm in diameter, and are tolerable to be exiting the mouth without irritating the lips. If desired, a transition tube may be utilized (not shown) that comprises a different size, configuration and/or function tube than the single or multi-lumen tube (i.e., one of the functions of the transition tube may be to connect to the negative pressure machine). The transition adaptor may be a component that facilitates the transition between the single or multi-lumen tube to the transition tube.

In other embodiments, oral appliances can be constructed that desirably direct a therapeutic vacuum or negative pressure to an oral wound site, such as an anatomical location where an oral surgical procedure has occurred. In such cases, the oral appliance may be particularized for use at the wound site, which may include the creation of channels or cavities proximate to the surgical location. If desired, the oral appliance may include features to accommodate the surgical removal of tissues (i.e., subsequent to wisdom tooth removal and/or root canal procedures), the surgical addition of tissues (i.e., to accommodate a bone implant or tissue graft), or may be modified in some manner (including as described herein) to accommodate inflamed and/or swollen tissues. In a similar manner, negative pressure oral systems, devices and methods could have significant utility in the treatment of oral wounds resulting from injuries. If desired, the oral appliances described herein may be utilized to prepare an area for surgery (i.e., to reduce inflammation and/or control infection in tissues targeted for surgery and/or adjacent to intended surgical sites) as well as to treat and/or manage surgical sites after surgical procedures. In various embodiments, such devices may be utilized in treating surgical anchor implant sites and/or grafting sites, where healing of the site is desirous prior to final implantation of a surgical implant and/or graft, as well as after the surgical procedure to promote healing of affected tissues.

Given that bruxism, or involuntary clenching of the teeth, is a risk factor for stress and potential damage to the periodontal ligaments due to high occlusal pressures (i.e., including causing or contributing to cellular hypoxia), the presence of the oral appliance could in various additional embodiments add an element of intraoral neuromuscular feedback, which could favorably decrease this involuntary clenching.

In various embodiments, a negative pressure vacuum machine may be provided that is equipped with one or more custom features particular to the present invention, or the system may simply incorporate use of a commercially available negative pressure/vacuum machine and/or attachment to an installed (I.e., permanent or semi-permanent) vacuum source. For example, a portable suction machine can be used with various embodiments of the present invention (i.e., many hospitals carry a wide variety of vacuum devices—from various manufacturers). A suitable portable suction machine may include minimal controls, such as delivering a negative pressure range of 25-250 mmHg, have continuous and intermittent operation cycles, may be rechargeable, and may be of low weight (i.e., approx. 5 lbs. or less, as opposed to the hospital based suction units that weigh upwards of 25 lbs.). Alternatively, a custom negative pressure/vacuum machine may be provided having more convenient features such as portability (i.e., including ultra-light weight components), battery power or rechargeable batteries, with design for single use, operator comfort, and be lightweight with ergonomic features. One exemplary pressure could be between 25 and 50 mmHg, which could be continuous or intermittent.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, with all manner of combinations of the various elements which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. An oral appliance for attachment to a negative pressure source, comprising:
    an elongated orthosis which allows normal respiration of a patient through a mouth of the patient without aid of an external device, the elongated orthosis having a generally U-shaped cross-section with an anterior region, an intermediate region and a lingual region,
    the anterior region having a first surface portion, the first surface portion substantially matching at least a portion of an anterior surface of a patient's dentition,
    the lingual region having a second surface portion that substantially matches at least a portion of a lingual surface of the patient's dentition,
    the anterior and lingual regions separated by the intermediate region; a first passage formed through at least a portion of the anterior region, a proximal end of the first passage in fluid communication with the negative pressure source; and
    a channel formed in the first surface portion of the anterior region, the channel located proximate to a gingival margin of the patient's dentition during use, the channel in fluid communication with a distal end of the first passage.

2. The oral appliance of claim 1, wherein the intermediate region includes an intermediate surface portion, the intermediate surface portion substantially matching at least a portion of an incisal surface of at least one tooth of the patient's dentition.

3. The oral appliance of claim 1, wherein the intermediate region includes an intermediate surface portion, the intermediate surface portion substantially matching at least a portion of an occlusal surface of at least one tooth of the patient's dentition.

4. The oral appliance of claim 1, wherein the anterior region further includes a third surface portion, the third surface portion substantially matching at least a portion of a gum tissue proximate to the patient's dentition, the channel being located between the first surface portion and the third surface portion.

5. The oral appliance of claim 4, wherein the first and second surface portions comprise a flexible material.

6. The oral appliance of claim 1, wherein the lingual region includes a second channel formed in the second surface portion, the second channel located proximate to a second gingival margin of the patient's dentition.

7. An oral appliance for attachment to a negative pressure source, comprising:
- a curved orthosis having a generally C-shaped cross-section with a first region, and a second region and a third region,
- the first region having a first contact surface, a portion of the first contact surface substantially matching at least a portion of a first tooth surface of a patient,
- the second region having a second contact surface, a portion of the second contact surface substantially matching at least a portion of a second tooth surface of the patient,
- the first and second regions separated by the third region;
- a first passage extending through the first region, a first end of the first passage in fluid communication with the negative pressure source; and
- a channel formed in the first region, the channel positioned over a location adjacent to a position of a gingival sulcus of the tooth of the patient, at least a portion of the channel in fluid communication with the first passage, the first region including a flexible surface which provides a fluid seal against a tissue surface of the patient to seal the channel and retain a negative pressure from the negative pressure source in local proximity to the gingival sulcus.

8. The oral appliance of claim 7, wherein the portion of the first contact surface substantially matches a facial surface portion of at least one tooth of the patient's dentition.

9. The oral appliance of claim 8, wherein the portion of the second contact surface substantially matches a lingual surface portion of the at least one tooth of the patient's dentition.

10. The oral appliance of claim 7, wherein the second region further includes a gum contact surface, at least a portion of the gum contact surface substantially matching and engaging with at least a portion of a gum tissue proximate to the first surface of the tooth.

11. The oral appliance of claim 10, wherein the first region spans a plurality of teeth of the patient.

12. The oral appliance of claim 10, wherein the channel spans a plurality of teeth of the patient.

13. The oral appliance of claim 7, wherein the third region includes a third contact surface, at least a portion of the third contact surface substantially matching at least an occlusal portion of a tooth of the patient.

14. An oral appliance for attachment to a negative pressure source, comprising:
- an elongated orthosis which does not substantially interfere with respiration of a patient through a mouth of the patient, the elongated orthosis having a generally U-shaped cross-section with an anterior region, an intermediate region and a lingual region,
- the anterior region having a first surface portion, the first surface portion substantially matching at least a portion of an anterior surface of a patient's dentition,
- the lingual region having a second surface portion that substantially matches at least a portion of a lingual surface of the patient's dentition,
- the anterior and lingual regions separated by the intermediate region;
- a first passage formed through at least a portion of the anterior region, a proximal end of the first passage in fluid communication with the negative pressure source; and
- a channel formed in at least one of the first and second surface portions, the channel positioned over a location matching a position of a gingival sulcus of the patient's dentition, the channel in fluid communication with a distal end of the first passage, at least one of the anterior and lingual regions including at least one flexible surface which provides a fluid seal against a tissue surface of the patient to seal the channel and retain a negative pressure from the negative pressure source in local proximity to the gingival sulcus.

15. The oral appliance of claim 14, wherein the anterior region spans a plurality of teeth of the patient.

16. The oral appliance of claim 14, wherein the channel spans a plurality of teeth of the patient.

17. The oral appliance of claim 14, wherein the intermediate region includes a third surface portion that substantially matches at least a portion of an occlusal surface of the patient's dentition.

18. The oral appliance of claim 14, wherein the anterior, lingual and intermediate regions each comprise a flexible material.

19. The oral appliance of claim 14, wherein the anterior and lingual surfaces of the patient's dentition are on a single tooth.

20. The oral appliance of claim 14, wherein the elongated orthosis encompasses an entire dental arch of the patient.

* * * * *